(12) United States Patent
Dumic et al.

(10) Patent No.: US 7,569,549 B2
(45) Date of Patent: Aug. 4, 2009

(54) ISOSTRUCTURAL PSEUDOPOLYMORPHS OF 9-DEOXO-9A-AZA-9A-METHYL-9A-HOMOERYTHROMYCIN A

(75) Inventors: Miljenko Dumic, Zagreb (HR); Mladen Vinkovic, Cakovec (HR); Marina Oresic, Sesvete (HR); Ernest Mestrovic, Bjelovar (HR); Aleksandar Danilovski, Rijeka (HR); Alojz Dumbovic, Zagreb (HR); Zdravka Knezevic, Zagreb (HR); Gorjana Lazarevski, Zagreb (HR); Dominik Cincic, Zagreb (HR); Darko Filic, Zagreb (HR); Katica Lazaric, Zagreb (HR); Dejan Kresimir Bucar, Pusca (HR)

(73) Assignee: Pliva Hrvatska D.O.O., Zagreb (HR)

( * ) Notice: Subject to any disclaimer, the term of this patent is extended or adjusted under 35 U.S.C. 154(b) by 0 days.

(21) Appl. No.: 10/390,573

(22) Filed: Mar. 17, 2003

(65) Prior Publication Data

US 2004/0014951 A1  Jan. 22, 2004

Related U.S. Application Data

(60) Provisional application No. 60/394,705, filed on Jul. 8, 2002, provisional application No. 60/393,612, filed on Jul. 3, 2002.

(30) Foreign Application Priority Data

Mar. 18, 2002  (HR)  ............................ P 20020231 A

(51) Int. Cl.
A61K 31/70 (2006.01)
C07H 17/08 (2006.01)

(52) U.S. Cl. .......................................... 514/29; 536/7.4

(58) Field of Classification Search ................. 537/7.4; 536/18.5, 7.4; 514/29
See application file for complete search history.

(56) References Cited

U.S. PATENT DOCUMENTS

| | | | |
|---|---|---|---|
| 4,517,359 | A | 5/1985 | Kobrehel et al. |
| 6,420,537 | B1 * | 7/2002 | Bosch et al. ................ 536/7.4 |
| 6,528,492 | B1 | 3/2003 | de la Torre Garcia et al. |
| 6,586,576 | B2 | 7/2003 | Aronhime et al. |
| 6,703,372 | B1 * | 3/2004 | Centellas et al. ............. 514/29 |
| 6,861,413 | B2 | 3/2005 | Li et al. |
| 6,949,519 | B2 * | 9/2005 | Centellas et al. ............. 514/29 |
| 6,977,243 | B2 * | 12/2005 | Li et al. ..................... 514/29 |
| 7,309,782 | B2 | 12/2007 | Li et al. |
| 2003/0139583 | A1 | 7/2003 | Singh et al. |
| 2003/0162730 | A1 | 8/2003 | Li et al. |
| 2003/0165563 | A1 | 9/2003 | Murphy et al. |
| 2003/0190365 | A1 | 10/2003 | Fergione et al. |

FOREIGN PATENT DOCUMENTS

| | | |
|---|---|---|
| CN | 116971 | 10/1997 |
| CN | 1205338 | 1/1999 |

(Continued)

OTHER PUBLICATIONS

Ognjen Čulić et al., Anti-inflammatory effects of macrolide antibiotics, European Journal of Pharmacology 429:209-229 (2001).
Ognjen Čulić et al., Azithromycin modulates neutrophil function and circulating inflammatory mediators in healthy human subjects, European Journal of Pharmaclogy 450:277-289 (2002).

(Continued)

*Primary Examiner*—Elli Peselev
(74) *Attorney, Agent, or Firm*—Sterne Kessler Goldstein & Fox, PLLC

(57) ABSTRACT

Substantially pure isostructural pseudopolymorphs of 9-deoxo-9a-aza-9a-methyl-9a-homoerythromycin A having the Formula I:

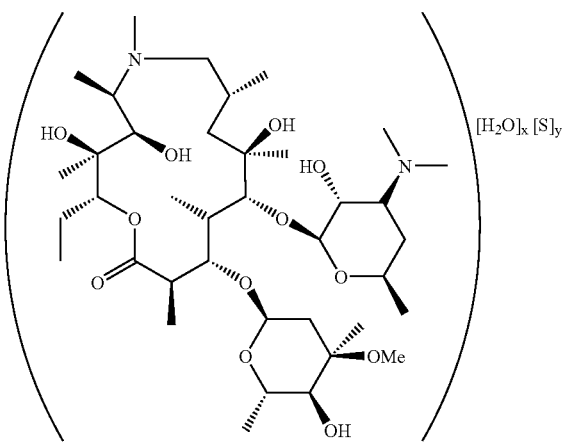

(I)

wherein S is an organic solvent which is at least partially miscible with water, x is 1, 1.25, 1.5 or 2, y is 0, 0.5, or 1, the pseudopolymorph being characterized by the monoclinic space group P2₁ and average unit cell parameters comprising: crystal axis lengths of a=15.5-17.0 Å, b=15.5-17.0 Å, and c=17.5-19.5 Å, and angles between the crystal axes of α=γ=90° and β=106°-112°. In addition, this disclosure is directed to processes for the preparation of the substantially pure isostructural pseudopolymorphs of Formula I; to pharmaceutical compositions containing substantially pure isostructural pseudopolymorphs of Formula I; and to a method for the treatment of bacterial and protozoan infections, and inflammation-related diseases by administration of a pharmaceutical composition containing the substantially pure isostructural pseudopolymorphs of Formula I.

6 Claims, 23 Drawing Sheets

FOREIGN PATENT DOCUMENTS

| | | |
|---|---|---|
| EP | 0677530 | 10/1995 |
| EP | 0 941 999 | 9/1999 |
| EP | 0984020 | 3/2000 |
| WO | WO-94/26758 A1 | 11/1994 |
| WO | WO 99/58541 * | 11/1999 |
| WO | WO-02/42315 A1 | 5/2002 |
| WO | WO-02/085898 A1 | 10/2002 |
| WO | WO-02/087596 A2 | 11/2002 |
| WO | WO-02/094843 A1 | 11/2002 |
| WO | WO-03/053399 A2 | 7/2003 |
| WO | WO-03/063838 A1 | 8/2003 |
| WO | WO-03/077830 A1 | 9/2003 |
| WO | WO-03/082889 A1 | 10/2003 |
| WO | WO-03/102009 A1 | 12/2003 |

OTHER PUBLICATIONS

F. Scaglione and G. Rossoni, Comparative anti-inflammatory effects of roxithromycin, azithromycin and clarithromycin, Journal of Antimicrobial Chemotherapy 41, Suppl. B, 47-50 (1998).

M.T. Labro, Anti-inflammatory activity of macrolides: a new therapeutic potential? Journal of Antimicrobial Chemotherapy 41, Suppl. B, 37-46 (1998).

* cited by examiner

Crystal Packing Of 9-deoxo-9a-aza-9a-methyl-9a-homoerythromycin A Dihydrate (Structure Coded GEGJAD Described In Cambridge Crystallographic Data Base)

Crystal Packing Of A New Isostructural Pseudopolymorph Of
9-deoxo-9a-aza-9a-methyl-9a-homoerythromycin
A Of The General Formula I (Ia: X = 1, Y = 0)

Crystal Packing Of A New Isostructural Pseudopolymorph Of
9-deoxo-9a-aza-9a-methyl-9a-homoerythromycin
A Of The General Formula I (Ib: S = Methanol, X = 1.25; Y = 1)

Crystal Packing Of A New Isostructural Pseudopolymorph Of
9-deoxo-9a-aza-9a-methyl-9a-homoerythromycin
A of The General Formula I (Ic: S = Ethanol, X = 1; Y = 0.5)

Crystal Packing Of A New Isostructural Pseudopolymorph
Of 9-Deoxo-9a-Aza-9a-Methyl-9a-Homoerythromycin A Of
The General Formula I (Id: S = *N*-Propanol, X = 1; Y = 0.5)

Crystal Packing Of A New Isostructural Pseudopolymorph Of 9-Deoxo-9a-Aza-9a-Methyl-9a-Homoerythromycin A Of The General Formula I (Ie: S = *Iso*-Propanol, X = 1.5; Y = 0.5)

Crystal Packing Of A New Isostructural Pseudopolymorph
Of 9-Deoxo-9a-Aza-9a-Methyl-9a-Homoerythromycin A Of
The General Formula I (If: S = *N*-Butanol, X = 1.5; Y = 0.5)

Crystal Packing Of A New Isostructural Pseudopolymorph Of
9-deoxo-9a-aza-9a-methyl-9a-homoerythromycin A Of
The General Formula I (Ig: S = *Iso*-Butanol, X = 1.25; Y = 0.5)

Crystal Packing Of A New Isostructural Pseudopolymorph
Of 9-deoxo-9a-aza-9a-methyl-9a-homoerythromycin A Of
The General Formula I (Ih: S = 1,2-Ethanediol, X = 1; Y = 0.5)

Crystal Packing Of A New Isostructural Pseudopolymorph Of
9-deoxo-9a-aza-9a-methyl-9a-homoerythromycin A Of
The General Formula I (Ii: S = 1,3-Propanediol, X = 1; Y = 0.5)

Crystal Packing Of A New Isostructural Pseudopolymorph
Of 9-deoxo-9a-aza-9a-methyl-9a-homoerythromycin A Of
The General Formula I (Ij: S = Glycerol, X = 1; Y = 0.5)

Crystal Packing Of A New Isostructural Pseudopolymorph Of 9-deoxo-9a-aza-9a-methyl-9a-homoerythromycin A Of The General Formula I (Ik: S = Glycerol, X = 1.5; Y = 0.5)

Crystal Packing Of A New Isostructural Pseudopolymorph Of 9-deoxo-9a-aza-9a-methyl-9a-homoerythromycin A Of The General Formula I (II: S = Acetone, X = 1; Y = 0.5)

Crystal Packing Of A New Isostructural Pseudopolymorph Of
9-deoxo-9a-aza-9a-methyl-9a-homoerythromycin A Of The
General Formula I (Im: S = Dimethyl Sulfoxide, X = 1; Y = 0.5)

Cavity Formation Within Unit Cell of
Isostructural Pseudopolymorph of
9-deoxo-9a-aza-9a-methyl-9a-homoerythomycin
A of General F rmula I SEM of the Surface of the
Pseudopolymorph of Formula Ia (x=1, y=0)

SEM of the Surface of the
Pseudopolymorph of Formula Ia (x=1, y=0)

Dissolution Rate of a New Isostructural Pseudopolymorph of 9-deoxo-9a-aza-9a-methyl-9a-homoerithromycin A of The General Formula I (Ia: x = 1, y = 0) (Batches 1-3, Example 19) compared with 9-deoxo-9a-aza-9a-methyl-9a-homoerithromycin A Dihydrate in The Medium pH 3 at 37 °C Dissolution Rate of a New Isostructural Pseudopolymorph of 9-deoxo-9a-aza-9a-methyl-9a-homoerithromycin A of The General Formula I (Ia: x = 1, y = 0) (Batches 1-3, Example 19) compared with 9-deoxo-9a-aza-9a-methyl-9a-homoerithromycin A Dihydrate in The Medium pH 6 at 37 C Dissolution Rate of a New Isostructural Pseudopolymorph of 9-deoxo-9a-aza-9a-methyl-9a-homoerythromycin A of The General Formula I (Ik: S = glycerol, x = 1.5, y=0.5) compared with 9-deoxo-9a-aza-9a-methyl-9a-homoerythromycin A Dihydrate in The Medium pH 6 at 37 C

ISOSTRUCTURAL PSEUDOPOLYMORPHS OF 9-DEOXO-9A-AZA-9A-METHYL-9A-HOMOERYTHROMYCIN A

Under 35 U.S.C. § 119(e), this application claims the benefit of prior U.S. Provisional Application No. 60/394,705, filed Jul. 8, 2002, and prior U.S. Provisional Application No. 60/393,612, filed Jul. 3, 2002, the entire contents of which are incorporated herein by reference.

Under 35 U.S.C. § 119, this application claims priority from Croatian Patent Application No. P20020231A, filed Mar. 18, 2002.

FIELD OF THE INVENTION

This invention relates to new isostructural pseudopolymorphs of 9-deoxo-9a-aza-9a-methyl-9a-homoerythromycin A, to a process for the preparation of such pseudopolymorphs, to pharmaceutical formulations incorporating the same and to methods of use of such formulations in the treatment of bacterial and protozoan infections, and inflammation-related diseases.

BACKGROUND OF THE INVENTION 9-deoxo-9a-aza-9a-methyl-9a-homoerythromycin A is the first and still the only marketed 15-membered semi-synthetic macrolide antibiotic from the group of azalides [The Merck Index, 12$^{th}$ Ed. (1996), p. 157 (946)]. It has the formula

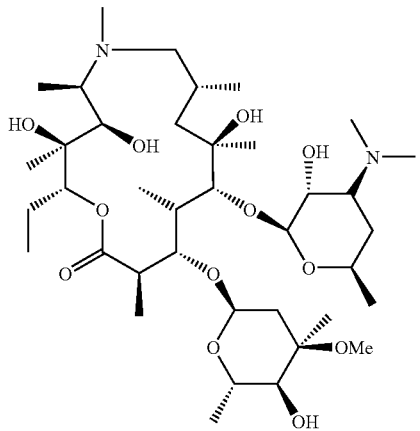

The synthesis of 9-deoxo-9a-aza-9a-methyl-9a-homoerythromycin A is described in U.S. Pat. No. 4,517,359. Its antibacterial spectrum (J. Antimicrob. Chemother., 1987, 19, 275), mode of action (Antimicrob. Ag. Chemother., 1987, 31, 1939) and pharmacology (J. Antimicrob. Chemother. 1993, 31, Suppl. E, 1-198) are well known.

9-deoxo-9a-aza-9a-methyl-9a-homoerythromycin A occurs in amorphous form, and in several different crystal forms characterized by different arrangements of the atoms in the crystal network. Most of the forms are crystalline, their crystal unit cells containing, in addition to 9-deoxo-9a-aza-9a-methyl-9a-homoerythromycin A, different numbers of water molecules and/or solvent molecules (pseudopolymorphs).

Anhydrous amorphous 9-deoxo-9a-aza-9a-methyl-9a-homoerythromycin A, having a melting point of 113-115° C., is described in U.S. Pat. No. 4,517,359. It may be obtained by evaporation of the solvent from a chloroform solution of crude 9-deoxo-9a-aza-9a-methyl-9a-homoerythromycin A. It is not crystalline but rather an amorphous product, resembling a solid foaming mass. A pure laboratory scale product may be obtained, either by chromatography of the crude final product or by dissolution of pure crystalline 9-deoxo-9a-aza-9a-methyl-9a-homoerythromycin A monohydrate or dihydrate in an organic solvent, followed by evaporation of the solvent. Pure amorphous anhydrous 9-deoxo-9a-aza-9a-methyl-9a-homoerythromycin A may be thus obtained. This procedure is not suitable for large-scale manufacture.

The preparation of various amorphous, crystalline solvated and hydrated forms of 9-deoxo-9a-aza-9a-methyl-9a-homoerythromycin A has been described in the patent literature. See, for example, U.S. Pat. No. 4,474,768; U.S. Pat. No. 6,245,903; EP 1 103 558; CN 1 093370; CN 1 161971; WO 99/58541; WO 00/32203; WO 01/00640; WO 02/09640; WO 02/10144; WO 02/15842; WO 02/10181 and WO 02/42315. Materials so produced have been subject to various disadvantages including lack of purity, instability, hygroscopicity, and the like.

Non-hygroscopic 9-deoxo-9a-aza-9a-methyl-9a-homoerythromycin A dihydrate was prepared as early as the mid-1980's by neutralization of an acidic solution of 9-deoxo-9a-aza-9a-methyl-9a-homoerythromycin A in an acetone-water mixture. Its crystal structure (single crystal) was evaluated upon recrystallization from ether, and was characterized by the orthorhombic space group P $2_12_12_1$. The unit cell parameters, namely crystal axes a=17.860 Å, b=16.889 Å and c=14.752 Å, and the angles between the crystal axes, $\alpha=\beta=\gamma=90°$, were published in 1987 at the Meeting of Chemists of Croatia (Book of Abstracts, Meeting of Chemists of Croatia, Feb. 19-20, 1987, p. 29). Thereafter, its crystal structure and preparation were described in detail (J. Chem. Res. (S), 1988, 152, Ibid., miniprint 1988, 1239; received Jun. 4, 1987; Cambridge Crystallographic Data Base: GEGJAD).

Subsequently, in U.S. Pat. No. 6,268,489 9-deoxo-9a-aza-9a-methyl-9a-homoerythromycin A dihydrate was described. That patent disclosed the preparation of the dihydrate by crystallization from tetrahydrofuran and hexane with the addition of water. The product thus formed is crystalline and can be obtained on a commercial scale in pure form. Its preparation is however subject to several disadvantages associated with the use of water-immiscible, toxic organic solvents and the necessity to carefully control the drying thereof.

Other techniques for preparing the dihydrate have been disclosed in the patent literature, e.g., in U.S. Pat. No. 5,869,629; EP 0 941 999; EP 1 103 558; HR P 921491; WO 01/49697; and WO 01/87912. Various of the procedures described involve the precipitation of the dihydrate by recrystallization from water-miscible solvents by the addition of water. The products formed by these and other processes described in the literature are however subject to a number of distinct disadvantages, ranging from the necessity to treat pharmaceutically pure 9-deoxo-9a-aza-9a-methyl-9a-homoerythromycin A materials to the yield, purity and homogeneity of the products themselves. Indeed, products formed by various of the prior art techniques incorporate differing amounts of combined and adsorbed solvents and water, thus imparting inconsistent stability, purity, release and potency characteristics when incorporated in pharmaceutical formulations.

It is among the objects of the present invention to provide a number of new, isostructural pseudopolymorphs of 9-deoxo-9a-aza-9a-methyl-9a-homoerythromycin A of predetermined crystalline structures and which, by virtue of such structures, provide more consistent, predictable properties in pharmaceutical formulations.

SUMMARY OF THE INVENTION

This invention relates to new isostructural pseudopolymorphs of 9-deoxo-9a-aza-9a-methyl-9a-homoerythromycin A, having the formula I

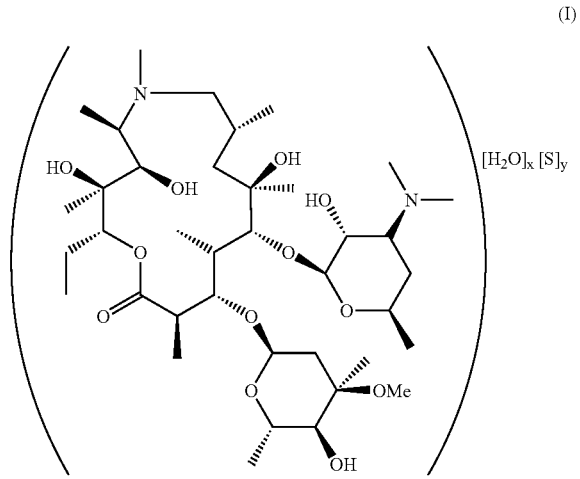

(I)

wherein

S is an organic solvent which is at least partially miscible with water, x is 1, 1.25, 1.5 or 2, y is 0, 0.5, or 1, the pseudopolymorphs being characterized by the monoclinic space group P $2_1$ and a range of unit cell parameters of crystal axis lengths from a=15.5-17.0 Å, b=15.5-17.0 Å and c=17.5-19.5 Å, and angles between the crystal axes of $\alpha=\gamma=90°$ and $\beta=106-112°$ The isostructural pseudopolymorphs hereof comprise the individual crystal entities identified as compounds Ia-Im in Table 1 below, whose crystal packing is illustrated in FIGS. 2-14 of the annexed drawings. As illustrated, they are compounds having unique crystal packing with discrete channel formation within their unit cells (see FIG. 15). As a consequence of the channel formation water and/or solvent molecules can be fitted into their cavities and removed upon drying to provide isostructural solid state forms, i.e., the pseudopolymorphs of the invention, which have unique crystalline structures as characterized by their monoclinic space group $P2_1$ and the lengths of their crystal axes and intermediate angles of their unit cells.

It is textbook knowledge that hydrates and/or solvates in general, of any compound should be defined as solid state forms that must have crystal water and/or solvent molecules in the asymmetric unit of the crystal unit cell besides the core compound moiety. Moreover, these hydrated and/or solvated molecules must be found in stoichiometric ratio to the core compound moiety, and are therefore clearly distinguishable from adsorbed water and/or solvent molecules.

X-ray crystallography is the only method that should be used as an analytically unambiguous and valid characterization of such hydrates and/or solvates. Various thermal methods (e.g. TGA or DSC) together with water and/or solvent content determinations (e.g., Karl Fischer water content determinations or GC) can only be used as a supplement to x-ray crystallographic data, and can give false and speculative results. Additionally, various literature data demonstrate that even a specific hydrate and/or solvate form can crystallize in different and distinct crystal entities, i.e., in distinct pseudopolymorphs. As an illustration a known antibiotic, nitrofurantoin, crystallizes in two distinct monohydrate solid state forms with exactly the same water content ($C_8H_6N_4O_5.H_2O$) but with clearly distinct crystallographic data, namely monohydrate I crystallizes in the monoclinic space group P $2_1$/n while monohydrate II crystallizes in the orthorhombic space group P bca (E. W. Pienaar, M. Caira, A. P. Lotter, J. Crystallogr. Spectrosc. Res 23 (1993) 739-744; CSDB codes HAXBUD and HAXBUD01).

Isostructural solid state forms, e.g., pseudopolymorphs, can have very similar or even identical powder diffraction patterns. Therefore, definite and unambiguous identification of any isostructural solid state forms, e.g. pseudopolymorphs, can and should be done by single crystal x-ray diffraction.

In accordance with the present invention, the specific crystalline structures of a group of stable isostructural pseudopolymorphs of 9-deoxo-9a-aza-9a-methyl-9a-homoerythromycin A have been determined, at least one of which pseudopolymorphs possesses a number of superior properties as compared with previously described forms of 9-deoxo-9a-aza-9a-methyl-9a-homoerythromycin A. In particular, one pseudopolymorph of the present invention, the isostructural 9-deoxo-9a-aza-9a-methyl-9a-homoerythromycin A pseudopolymorph of general formula I wherein x=1, y=0, possesses a number of superior properties as compared with the current commercially available form of 9-deoxo-9a-aza-9a-methyl-9a-homoerythromycin A, namely the dihydrate referred to hereinabove. Thus, that pseudopolymorph may, unlike the dihydrate, be reproducibly prepared under a wide range of preparative conditions. Second, it can be prepared directly from the native solution of crude 9-deoxo-9a-aza-9a-methyl-9a-homoerythromycin A, or from crude 9-deoxo-9a-aza-9a-methyl-9a-homoerythromycin A itself, rather than from any purified 9-deoxo-9a-aza-9a-methyl-9a-homoerythromycin A material. Third, this new pseudopolymorph may be prepared in high purity and pharmaceutically acceptable quality.

Fourth, the new pseudopolymorph is an air-stable, free-flowing form of 9-deoxo-9a-aza-9a-methyl-9a-homoerythromycin A (based on the granulated habit of its small crystals, see FIG. 16.). Fifth, the new pseudopolymorph has significantly better dissolution rates in both acid and neutral media as compared with the dihydrate. Sixth, the intrinsic dissolution rate (IDR) of the pseudopolymorph is significantly higher than the dissolution rate of the dihydrate. Seventh, the new pseudopolymorph may be used in the preparation of a variety of pharmaceutical preparations intended for immediate, controlled or sustained release applications. Finally, because of its superior dissolution characteristics this new pseudopolymorph, unlike the dihydrate or other previously known forms of 9-deoxo-9a-aza-9a-methyl-9a-homoerythromycin A, can be successfully utilized in the preparation of rapidly acting oral and local, particularly topical, pharmaceutical formulations.

The present invention further relates to a process for the preparation of the new isostructural 9-deoxo-9a-aza-9a-methyl-9a-homoerythromycin A pseudopolymorphs of Formula I, which process comprises:

(a) dissolving a 9-deoxo-9a-aza-9a-methyl-9a-homoerythromycin A material in (1) an organic solvent which is at least partially water-miscible, (2) a mixture of such organic solvents, (3) a mixture of the organic solvent and water or (4) a mixture of water and at least one mineral or organic acid;

(b) crystallizing the isostructural pseudopolymorph from the solution;

(c) isolating the isostructural pseudopolymorph; and (d) transforming the isostructural pseudopolymorph to a stable isostructural pseudopolymorph of Formula I wherein x=1 and y=0.

Finally, the present invention also relates to pharmaceutical formulations comprising the new isostructural pseudopolymorphs of 9-deoxo-9a-aza-9a-methyl-9a-homoerythromycin A in combination with one or more pharmaceutically acceptable carriers and other excipients, and to a method for the treatment of bacterial and protozoan infections, and inflammation-related diseases in humans or animals subject thereto, involving the administration of such pharmaceutical formulations to subjects in need of such treatment.

DETAILED DESCRIPTION OF THE INVENTION

Figure 1:
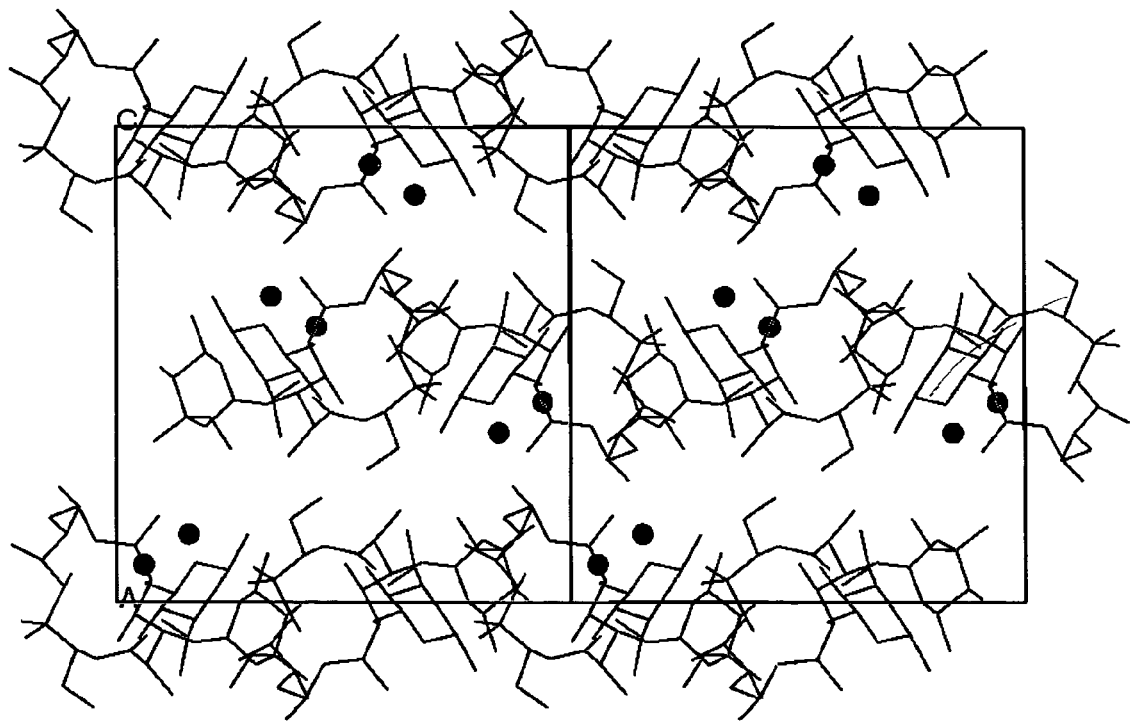
FIG. 1 is a crystal packing diagram of the current commercially-available 9-deoxo-9a-aza-9a-methyl-9a-homoerythromycin A dihydrate (the structure coded GEGJAD, described in the Cambridge Crystallographic database)
Figure 2:
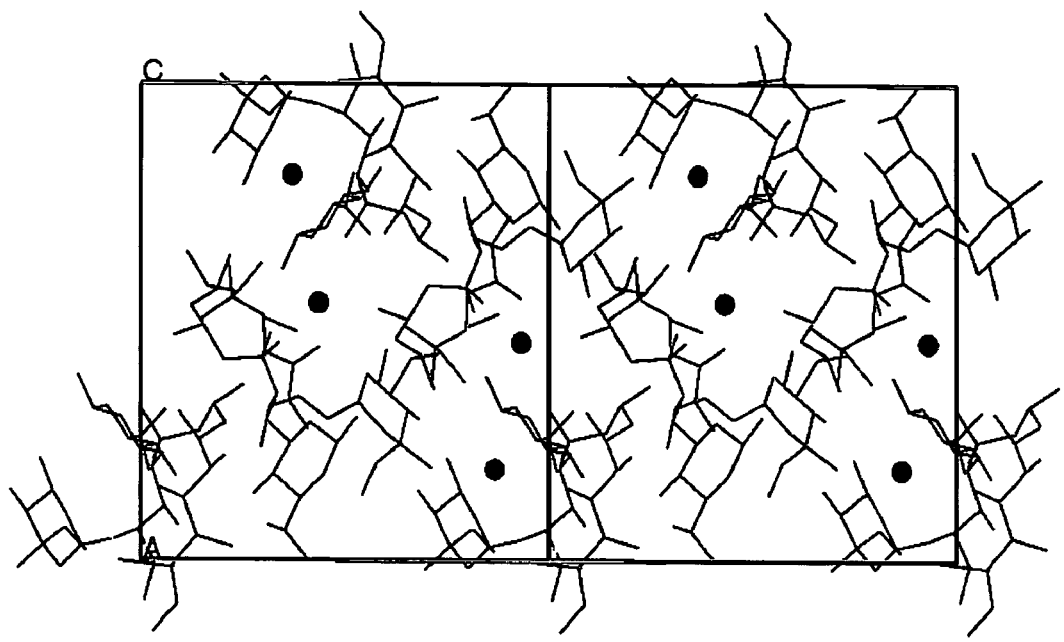
FIG. 2 is a crystal packing diagram of an isostructural pseudopolymorph of 9-deoxo-9a-aza-9a-methyl-9a-homoerythromycin A of Formula I (compound Ia: x=1, y=0)
Figure 3:
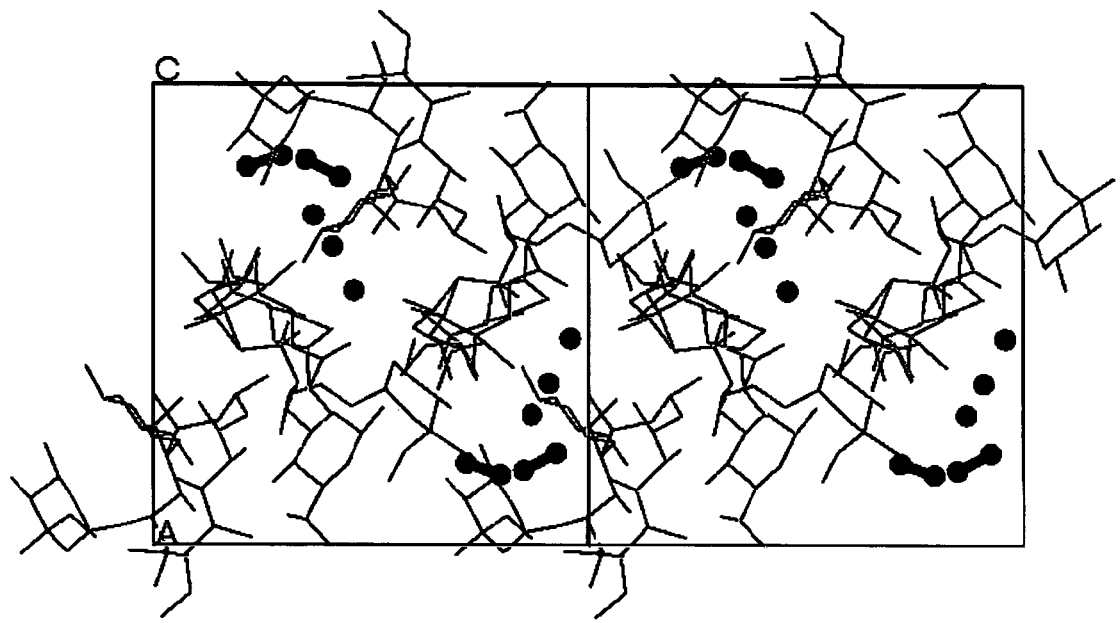
FIG. 3 is a crystal packing diagram of a further isostructural pseudopolymorph of 9-deoxo-9a-aza-9a-methyl-9a-homoerythromycin A of the invention (compound Ib: S=methanol; x=1.25, y=1)
Figure 4:
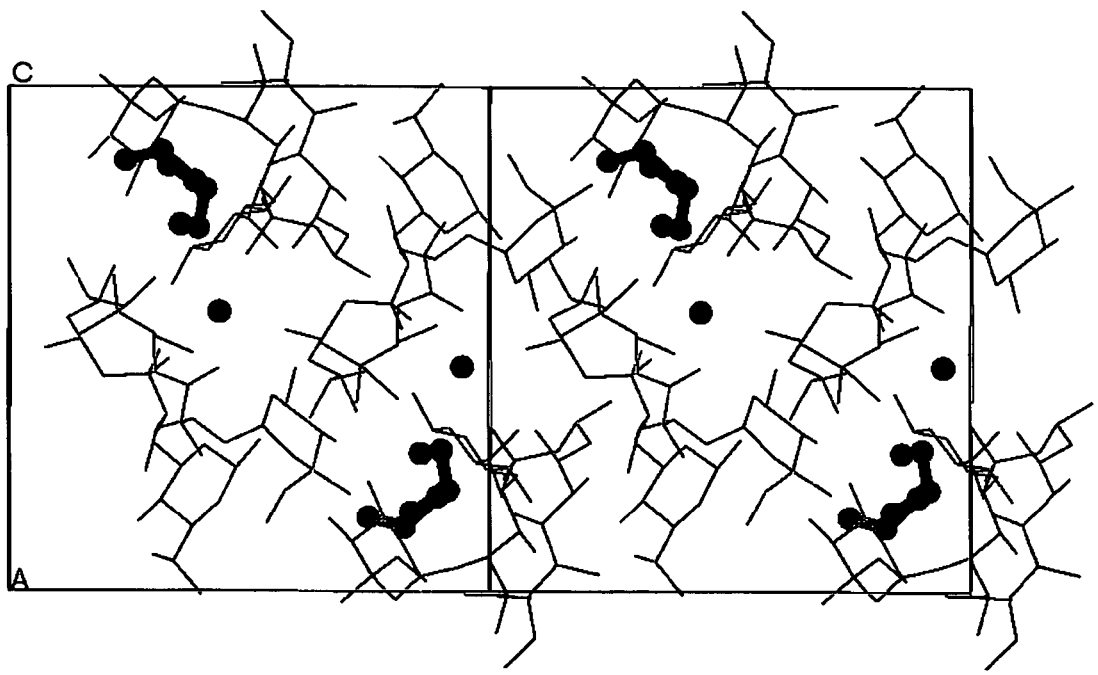
FIG. 4 is a crystal packing diagram of a further isostructural pseudopolymorph of 9-deoxo-9a-aza-9a-methyl-9a-homoerythromycin A of the invention (compound Ic: S=ethanol; x=1, y=0.5)
Figure 5:
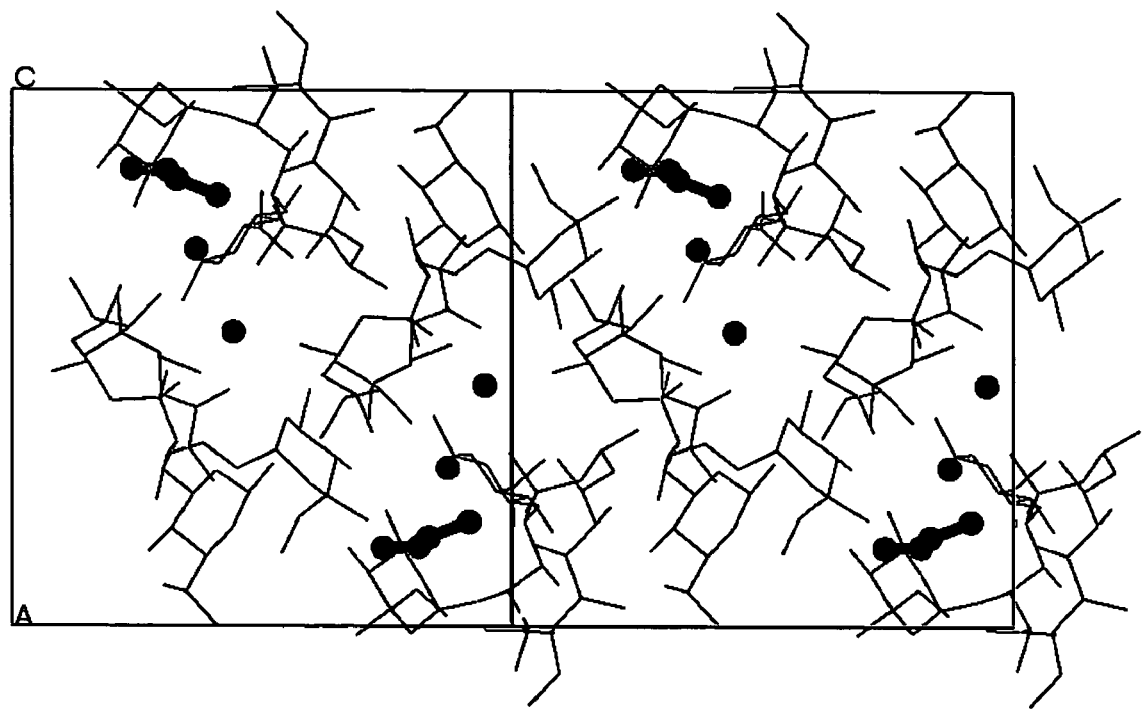
FIG. 5 is a crystal packing diagram of a further isostructural pseudopolymorph of 9-deoxo-9a-aza-9a-methyl-9a-homoerythromycin A of the invention (compound Id: S=n-propanol; x=1, y=0.5)
Figure 6:
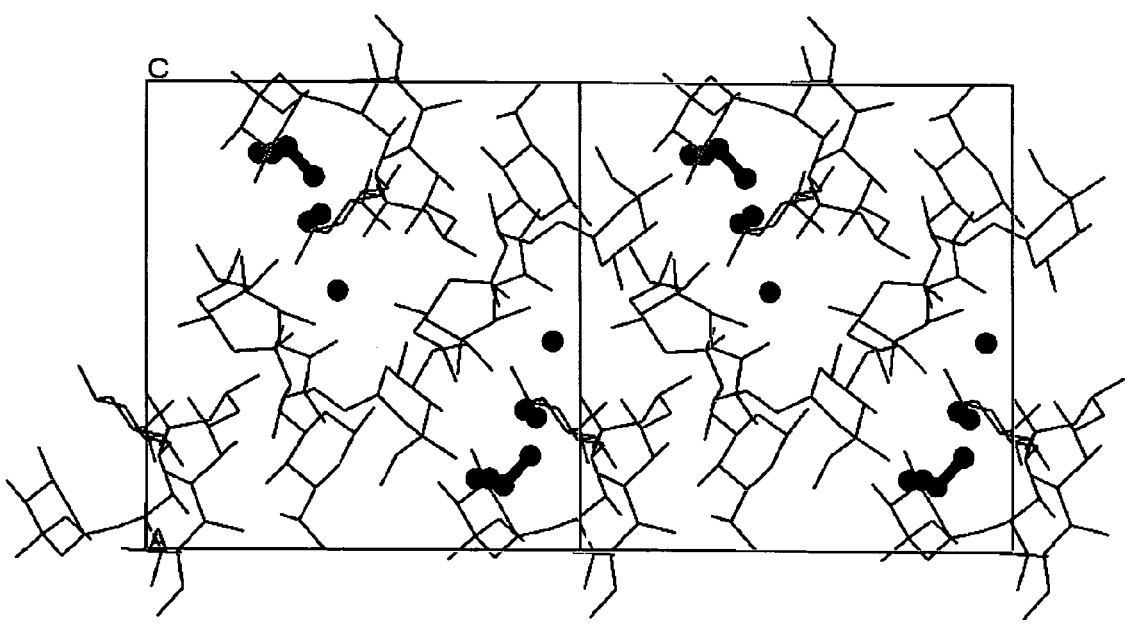
FIG. 6 is a crystal packing diagram of a further isostructural pseudopolymorph of 9-deoxo-9a-aza-9a-methyl-9a-homoerythromycin A of the invention (compound Ie S=isopropanol; x=1.5, y=0.5)
Figure 7:
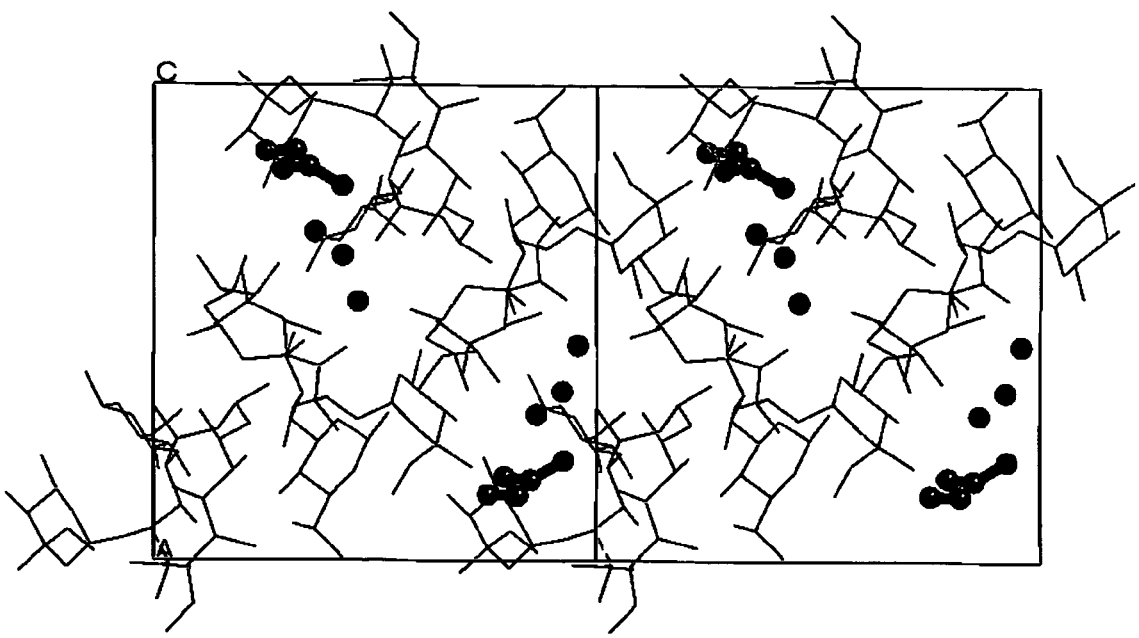
FIG. 7 is a crystal packing diagram of a further isostructural pseudopolymorph of 9-deoxo-9a-aza-9a-methyl-9a-homoerythromycin A of the invention (compound If: S=n-butanol; x=1.5, y=0.5)
Figure 8:
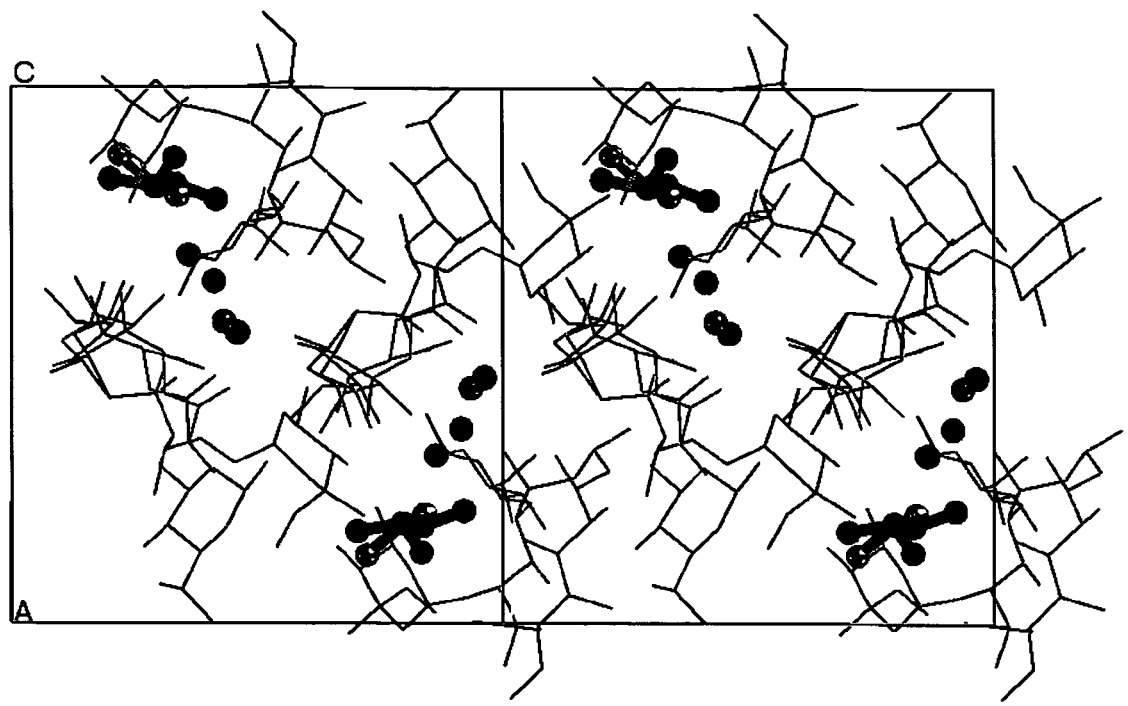
FIG. 8 is a crystal packing diagram of a further isostructural pseudopolymorph of 9-deoxo-9a-aza-9a-methyl-9a-homoerythromycin A of the invention (compound Ig: S=isobutanol; x=1.25, y=0.5)
Figure 9:
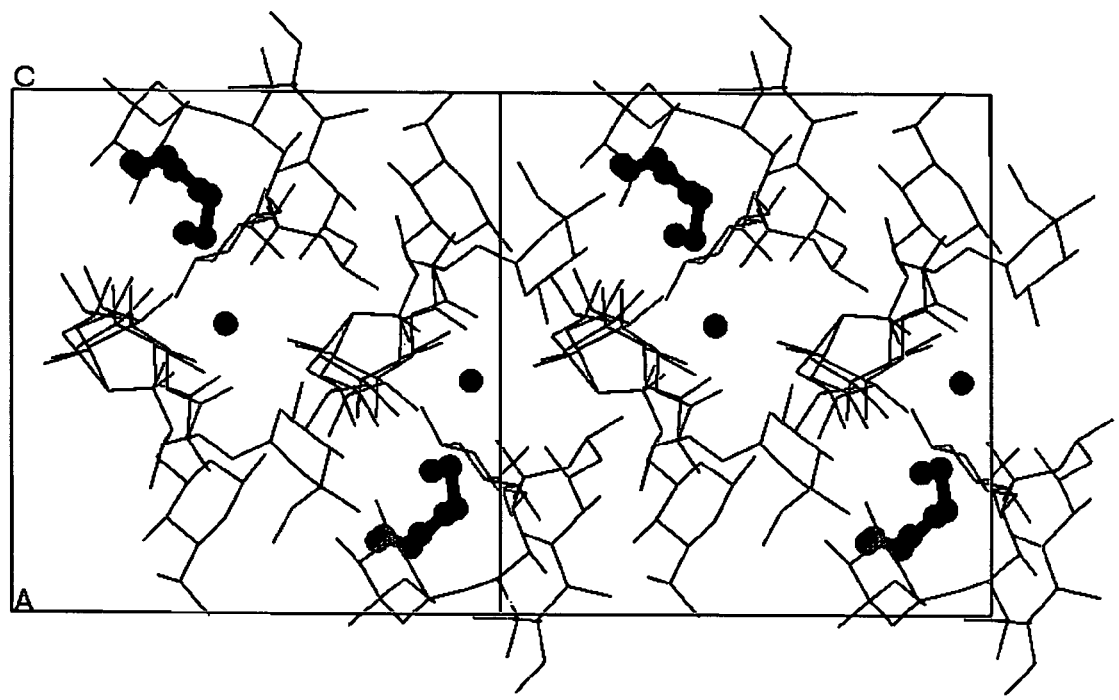
FIG. 9 is a crystal packing diagram of a further isostructural pseudopolymorph of 9-deoxo-9a-aza-9a-methyl-9a-homoerythromycin A of the invention (compound Ih: S=1,2-ethanediol; x=1, y=0.5)
Figure 10:
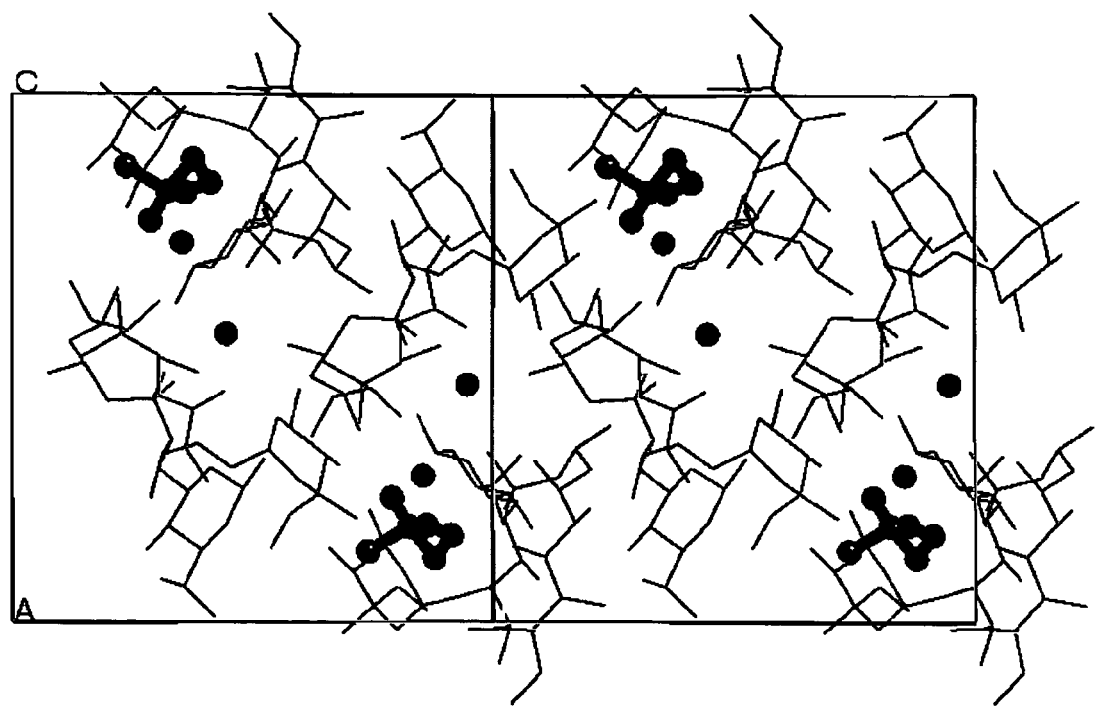
FIG. 10 is a crystal packing diagram of a further isostructural pseudopolymorph of 9-deoxo-9a-aza-9a-methyl-9a-homoerythromycin A of the invention (compound Ii: S=1,3-propanediol; x=1, y=0.5)
Figure 11:
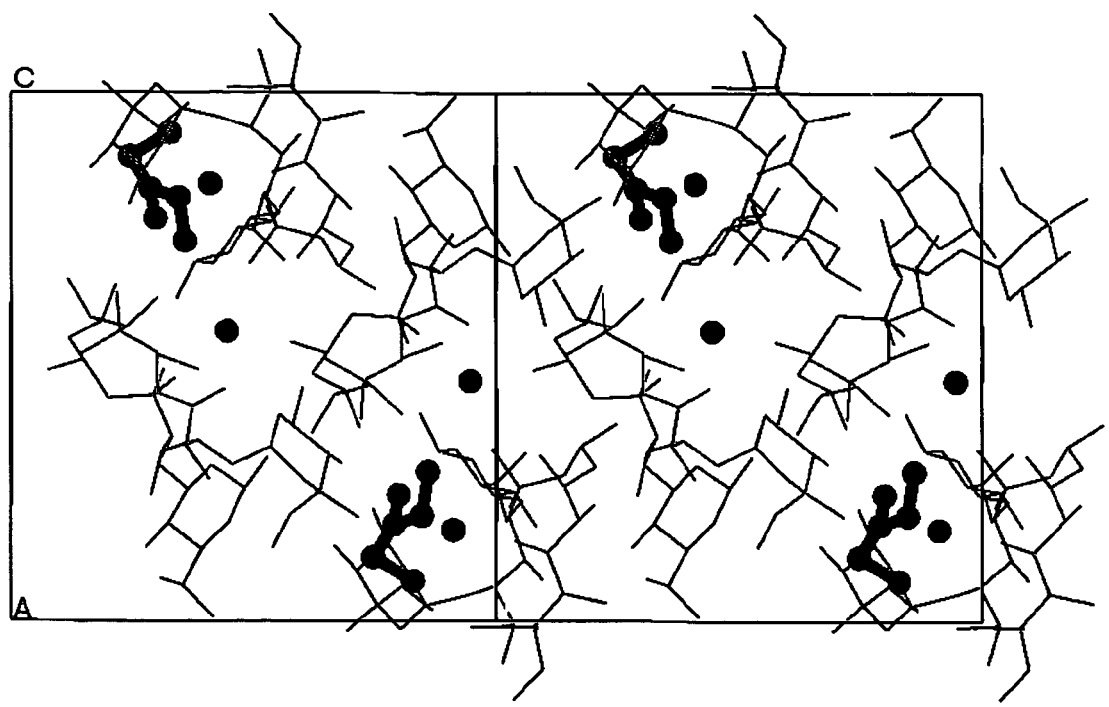
FIG. 11 is a crystal packing diagram of a further isostructural pseudopolymorph of 9-deoxo-9a-aza-9a-methyl-9a-homoerythromycin A of the invention (compound Ij: S=glycerol; x=1, y=0.5)
Figure 12:
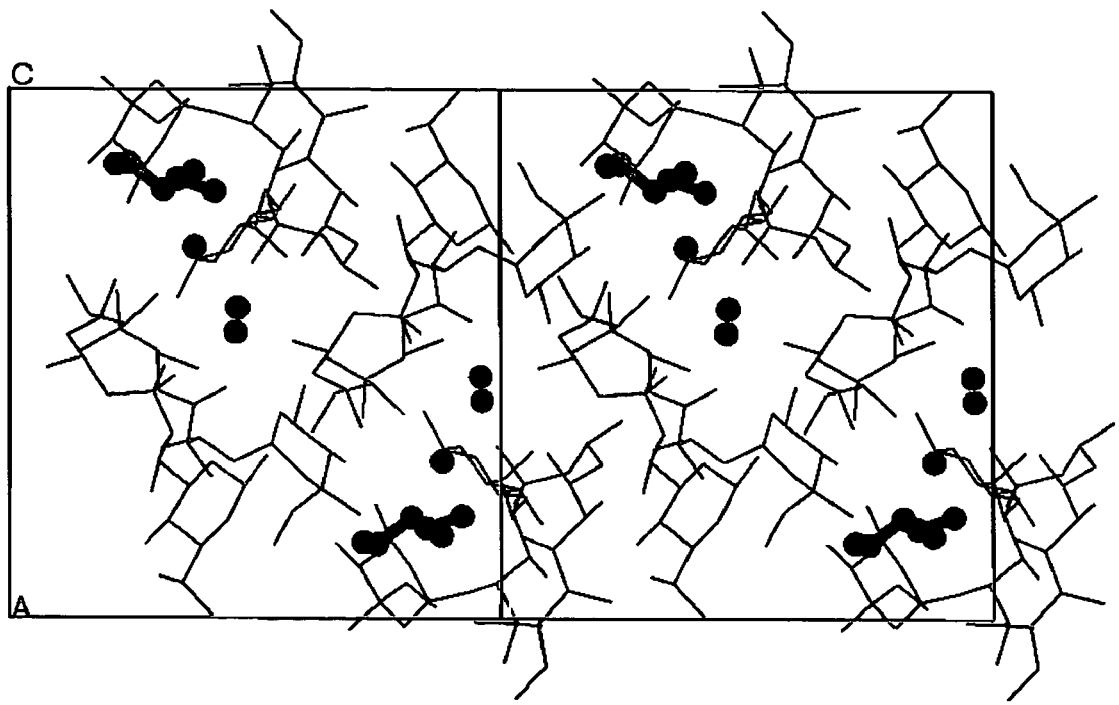
FIG. 12 is a crystal packing diagram of a further isostructural pseudopolymorph of 9-deoxo-9a-aza-9a-methyl-9a-homoerythromycin A of the invention (compound Ik: S=glycerol; x=1.5, y=0.5)
Figure 13:
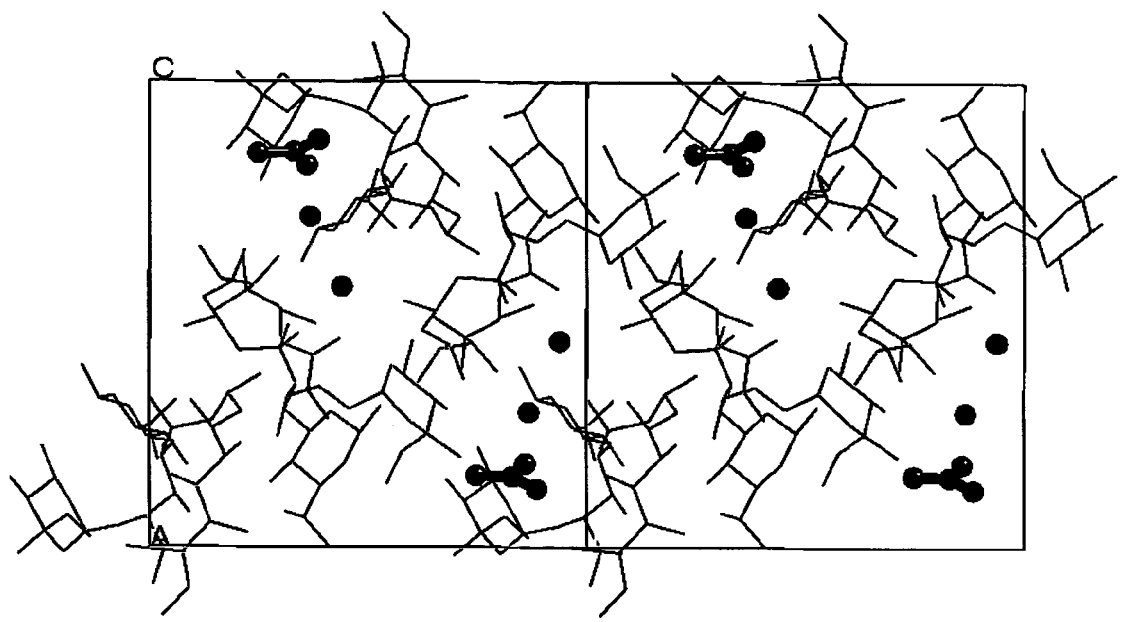
FIG. 13 is a crystal packing diagram of a further isostructural pseudopolymorph of 9-deoxo-9a-aza-9a-methyl-9a-homoerythromycin A of the invention (compound Il: S=acetone; x=1, y=0.5)
Figure 14:
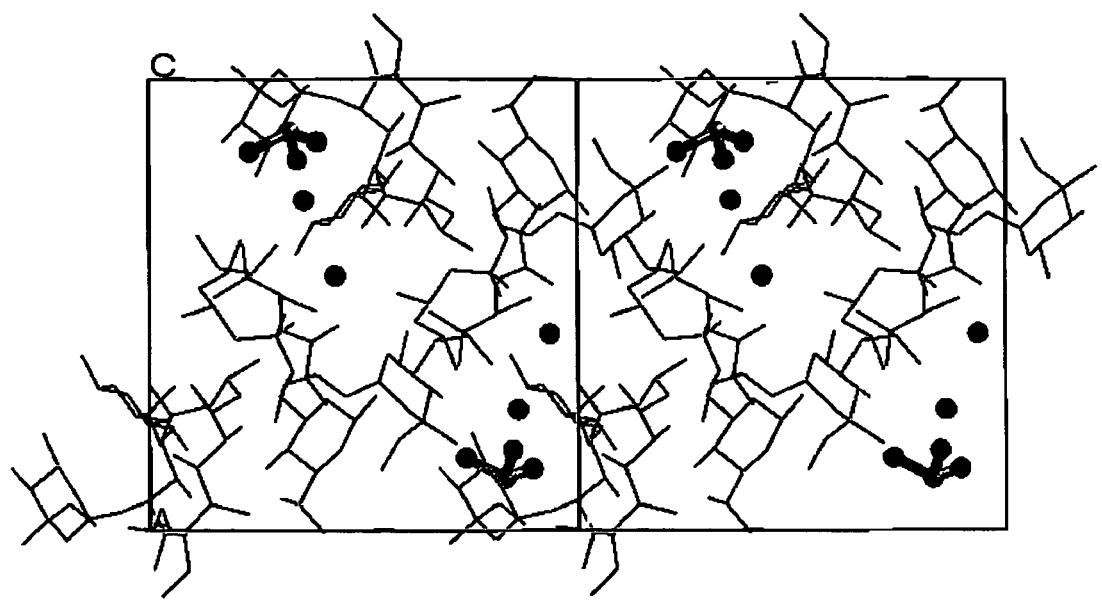
FIG. 14 is a crystal packing diagram of a further isostructural pseudopolymorph of 9-deoxo-9a-aza-9a-methyl-9a-homoerythromycin A of the invention (compound Im: S=dimethylsulfoxide (DMSO); x=1, y=0.5)
Figure 15:
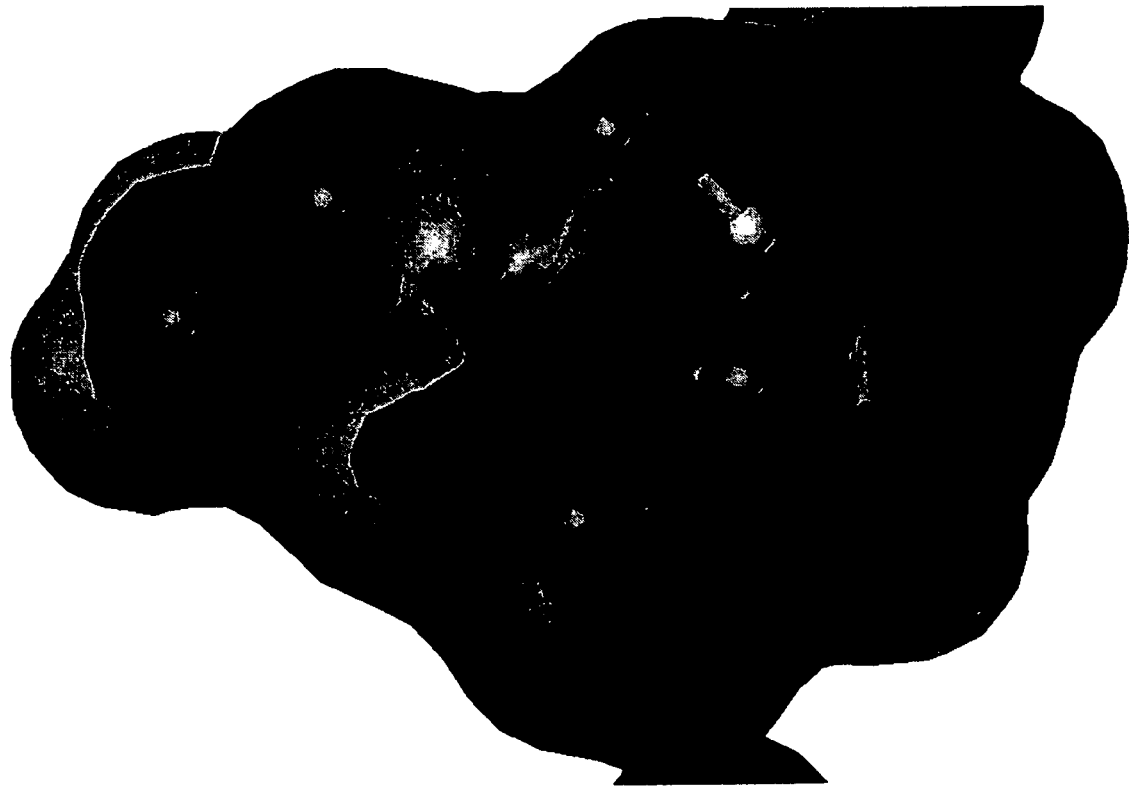
FIG. 15 is an illustration of channel formation within the unit cell of the isostructural pseudopolymorph of 9-deoxo-9a-aza-9a-methyl-9a-homoerythromycin A of general formula I.

As used herein with reference to the isostructural pseudopolymorphs of 9-deoxo-9a-aza-9a-methyl-9a-homoerythromycin A of the present invention, the term "substantially pure" denotes a pseudopolymorph of Formula I characterized by the monoclinic space group P $2_1$ and the average unit cell parameters identified above, that is at least 90% pure. To be more specific, the phrase "at least 90% pure" refers to the pseudopolymorphs of the present invention that contain no more than 10% of another compound, particularly not more than 10% of some other crystalline or amorphous form of 9-deoxo-9a-aza-9a-methyl-9a-homoerythromycin A. Preferably, the "substantially pure" pseudopolymorph of the present invention is "essentially pure," that is it contains 5% or less of any other compound or some other crystalline or amorphous form of 9-deoxo-9a-aza-9a-methyl-9a-homoerythromycin A.

In addition, as used herein, the term "9-deoxo-9a-aza-9a-methyl-9a-homoerythromycin A material" utilized in step (a) of the process for forming the isostructural pseudopolymorphs of 9-deoxo-9a-aza-9a-methyl-9a-homoerythromycin A hereof, refers to any form of 9-deoxo-9a-aza-9a-methyl-9a-homoerythromycin A, including crude or purified 9-deoxo-9a-aza-9a-methyl-9a-homoerythromycin A or a solvate or hydrate thereof, in either crystalline or amorphous form; or the "native solution" of 9-deoxo-9a-aza-9a-methyl-9a-homoerythromycin A formed during the last step of its syntheses (e.g. from 9-deoxo-9a-aza-9a-homoerythromycin A ("9a-DeMet"), as one of its last intermediates).

As used herein, the term "crude 9-deoxo-9a-aza-9a-methyl-9a-homoerythromycin A" is intended to include 9-deoxo-9a-aza-9a-methyl-9a-homoerythromycin A of any purity less than pharmaceutically acceptable purity, including 9-deoxo-9a-aza-9a-methyl-9a-homoerythromycin A obtained prior to final purification thereof.

As used herein, the term "native solutions of 9-deoxo-9a-aza-9a-methyl-9a-homoerythromycin A" refers to solutions of 9-deoxo-9a-aza-9a-methyl-9a-homoerythromycin A in water or any organic solvents, or admixtures thereof, utilized in the final step of preparing 9-deoxo-9a-aza-9a-methyl-9a-homoerythromycin A from its last intermediates (e.g. from 9a-DeMet), prior to isolation of crude 9-deoxo-9a-aza-9a-methyl-9a-homoerythromycin A.

9-Deoxo-9a-aza-9a-homoerythromycin A ("9a-DeMet") used as starting material in the presently claimed methods is also referred to in the art as 11-aza-10-deoxo-10-dihydro-erythromycin A (10-dihydro-10-deoxo-11-azaerythromycin A) (U.S. Pat. No. 4,328,334; J. Chem Res. (M) 1988, 1239). It is known and obtainable e.g. by conventional methods (see: U.S. Pat. No. 4,328,334; J. Chem. Soc., Perkin Trans. I 1986, 1881).

Solvents utilized in the native solutions of 9-deoxo-9a-aza-9a-methyl-9a-homoerythromycin A may include water, chlorinated solvents, e.g. haloalkanes having one or two carbon atoms such as chloroform or dichloromethane; esters of acetic acid with a $C_2$-$C_4$ lower alkyl group such as ethyl acetate, isopropyl acetate or n-butyl acetate; monohydric $C_2$-$C_4$ alkanols such as isopropanol or 2-butanol; $C_1$-$C_4$ ketones such as acetone or isobutylketone; or aromatic or substituted aromatic solvents such as toluene.

1. Preparation of the Pseudopolymorphs of the Invention

Step (a)—Dissolving the 9-deoxo-9a-aza-9a-methyl-9a-homoerythromycin A Material

As disclosed above, the 9-deoxo-9a-aza-9a-methyl-9a-homoerythromycin A material is dissolved in step (a) of the process for the preparation of the isostructural pseudopolymorphs of the invention in (1) an organic solvent which is at least partially water-miscible, (2) a mixture of such organic solvents, (3) a mixture of the organic solvent and water or (4) a mixture of water and at least one mineral or organic acid. Organic solvents which are so useful include lower aliphatic straight or branched-chain alkanols such as methanol, ethanol, n-propanol, isopropanol, n-butanol, iso-butanol, sec-butanol, tert-butanol or allyl alcohol; cycloalkanols, such as cyclopentanol or cyclohexanol; arylalkanols, such as benzyl alcohol; diols, such as 1,2-ethanediol, 1,2-propanediol, 1,3-propanediol, 1,4-butanediol or 2-butene-1,4-diol; triols, such as glycerol; ethers, such as diethyl ether, monoglyme, diglyme or 1,4-dioxane; ketones, such as acetone, 2-butanone; esters, such as methyl formate, ethyl formate, methyl acetate, ethyl acetate or ethyl lactate; amines, such as N-methylmorpholine, amides, such as dimethylformamide or dimethylacetamide; lactams, such as 2-pyrrolidone, N-methylpyrrolidone; ureas, such as N,N,N',N'-tetramethylurea; nitriles, such as acetonitrile or propionitrile; sulfoxides, such as dimethyl sulfoxide; or sulphones, such as sulfolane.

The mineral or organic acids which may be utilized for acidification employed in step (a) of the process for forming the pseudopolymorphs hereof may comprise any common mineral or organic acid. Suitable examples include, but are not limited to, hydrochloric, sulfuric, sulfurous, phosphoric, carbonic, formic, acetic, propionic, citric, tartaric, maleic, oxalic, chloroacetic, benzoic, methanesulfonic or p-toluene sulfonic acid.

The dissolution of the 9-deoxo-9a-aza-9a-methyl-9a-homoerythromycin A material in step (a) is carried out at temperatures of from about 0° to about 100° C., preferably at from about 0° to about 80° C. and, most desirably, at temperatures of from about 5° to about 60° C.

Step (b)—Crystallization of the Pseudopolymorphs

The new isostructural pseudopolymorphs of the invention are crystallized from the 9-deoxo-9a-aza-9a-methyl-9a-homoerythromycin A solution in step (b) of the process hereof by either controlled cooling, isothermal saturation of the solution with water until slight turbidity of the solution occurs, or by neutralization of the acidic solution with a common inorganic or organic base.

Inorganic bases which may be so utilized include common inorganic bases, such as the hydroxides, oxides or carbonates of Groups I or II of The Periodic Table Of The Elements, e.g., the alkali metal or alkaline earth metal bases such as lithium, sodium, potassium, barium, magnesium or calcium hydroxide; sodium, magnesium or calcium oxide; sodium or potassium carbonate; ammonia solutions. Organic bases which are so useful include organic amines, such as trimethylamine, triethylamine, piperidine, 3-methylpyridine, piperazine, triethanolamine or ethylene diamine; or quaternary organic hydroxides, such as tetramethyl-, tetraethyl- or tetrabutyl-ammonium hydroxide.

The crystallization may be carried out with or without crystal seeding i.e., by the addition of small amounts of one of the pseudopolymorphs of the present invention, in amounts of from about 0.1 to about 5.0% based on the amount of the initial 9-deoxo-9a-aza-9a-methyl-9a-homoerythromycin A material treated.

The crystallization, whether performed by controlled cooling, isothermal saturation or neutralization of the acidic solution with base, is carried out at temperatures of from about −10° C. to about 80° C., preferably from about 0° C. to about 40° C., and most desirably at temperatures of from about 5° C. to about 25° C. The crystallization is completed in a period of from about 30 minutes to about 7 days.

Step (c) Isolating the Isostructural Pseudopolymorphs

The crystalline isostructural pseudopolymorphs hereof are isolated in step (c) in conventional manner, e.g., by centrifugation, filtration or the like, operating under reduced, atmospheric or elevated pressures. The isolated pseudopolymorph is then washed in a water-miscible organic solvent (such as those described hereinabove) or in such a solvent admixed with water. The resulting intermediate product is then dried in conventional manner, e.g., by fluid bed drying, operating under atmospheric pressure at temperatures of from about 20° to about 120° C., or under reduced pressures of from about 2 to about 80 kPa and at temperatures of from about 30° C. to about 120° C.

Step (d)—Transforming the Isostructural Pseudopolymorph to a Stable Isostructural Pseudopolymorph of 9-deoxo-9a-aza-9a-methyl-9a-homoerythromycin A Formula I wherein x=1 and y=0

Finally, transformation of the crystalline dried (or wet) isostructural pseudopolymorph of Formula I formed in step (b) to the pseudopolymorph Ia (x=1, y=0) is carried out by removal of solvent and excess water by lyophilization, or by drying under reduced pressures of from about 0.01 to about 80 kPa or at atmospheric pressure and temperatures of from about −100° to about 120° C.

Figure 16A:
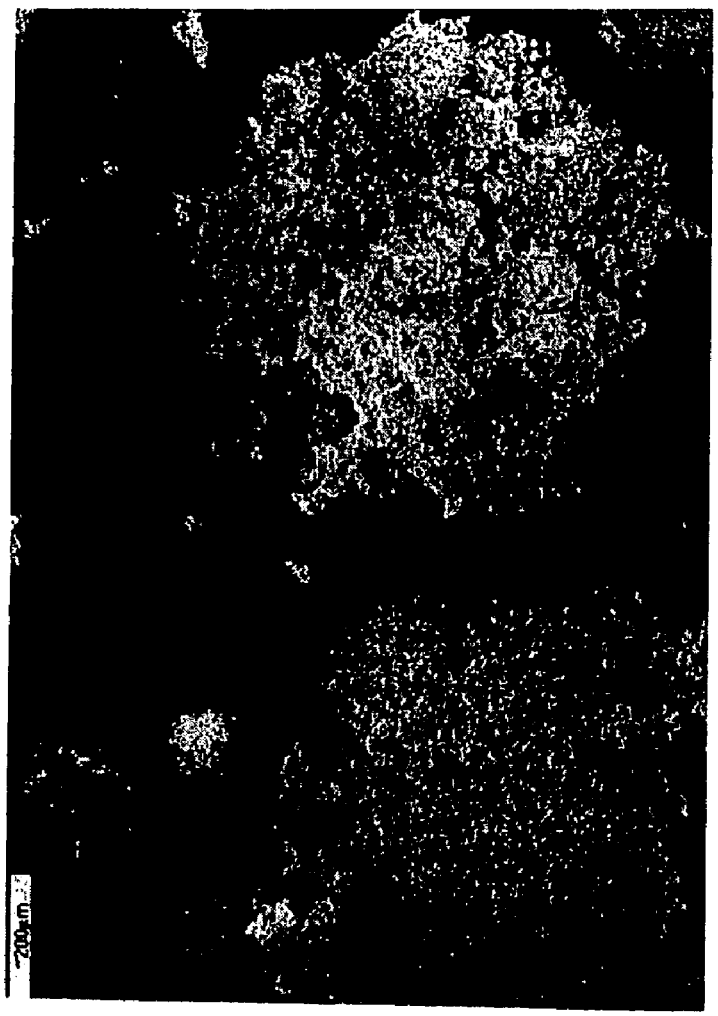
FIG. 16 is an SEM of the surface of the isostructural pseudopolymorph of 9-deoxo-9a-aza-9a-methyl-9a-homoerythromycin A of Formula I (compound Ia: x=1, y=0)
Figure 16B:
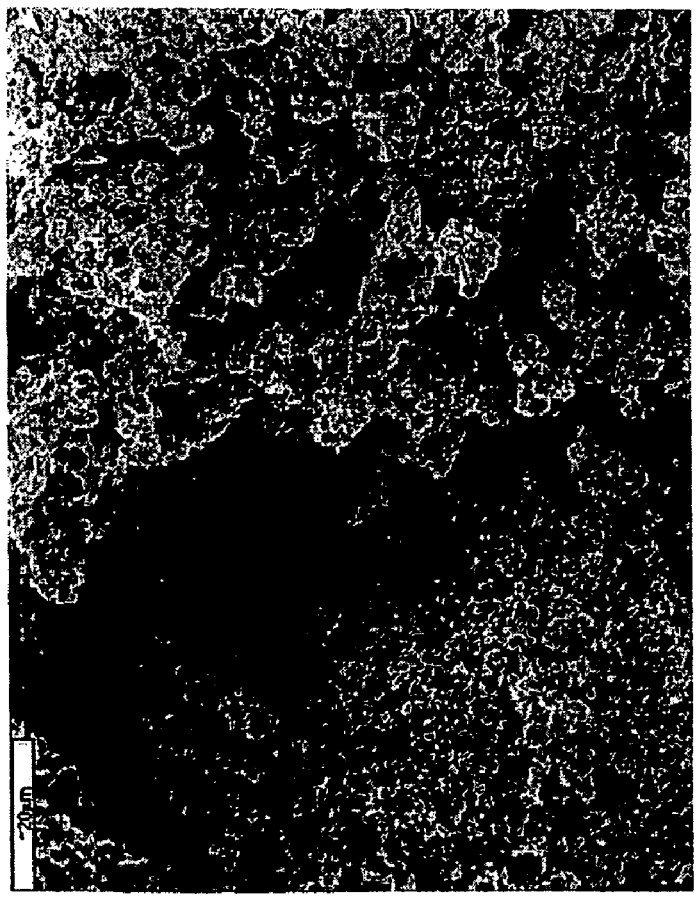
Figure 19:
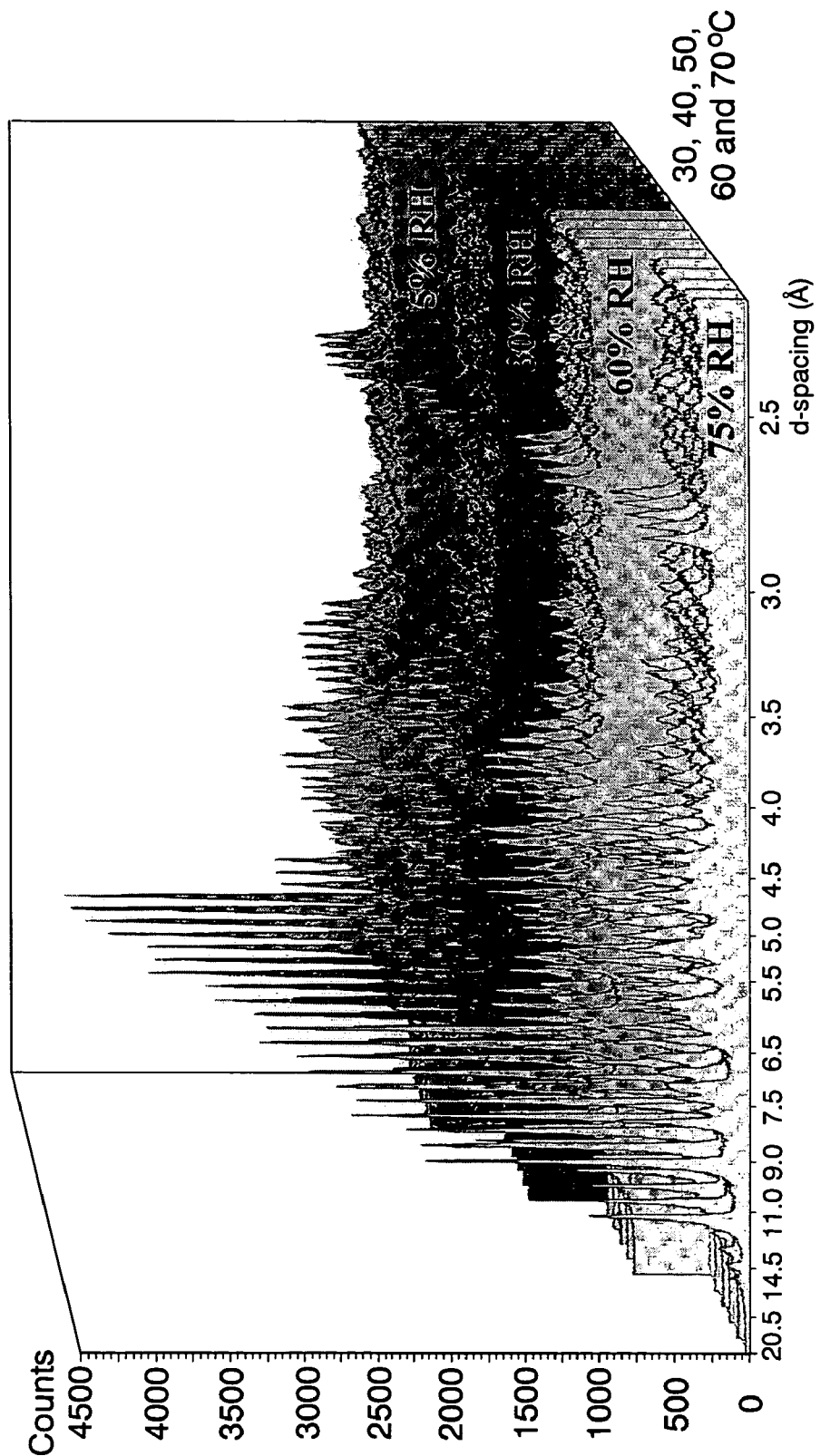
FIG. 19 is a graph illustrating the solid state stability of the isostructural pseudopolymorph of 9-deoxo-9a-aza-9a-methyl-9a-homoerythromycin A of Formula I (compound Ia: x=1, y=0) under various stress conditions (temperatures from 30°-70° C., and humidities from 5-75% RH).

The new isostructural pseudopolymorph of 9-deoxo-9a-aza-9a-methyl-9a-homoerythromycin A of general formula I wherein x=1, y=0, produced by the process of this invention in at least substantial purity, possesses good flowability, porous crystal structure (see FIG. 16.) and excellent stability characteristics under varying humidity conditions (see FIG. 19.). The improved properties of that pseudopolymorph relative to the commercially available 9-deoxo-9a-aza-9a-methyl-9a-homoerythromycin A dihydrate are more fully disclosed in Examples 25-27 below.

2. Formulations of the Pseudopolymorphs of the Invention

The new isostructural 9-deoxo-9a-aza-9a-methyl-9a-homoerythromycin A pseudopolymorphs of the present invention can be utilized in the preparation of rapid, controlled and sustained release pharmaceutical formulations, suitable for oral, rectal, parenteral, transdermal, buccal, nasal, sublingual, subcutaneous or intravenous administration. Such formulations may be useful for the treatment of bacterial and protozoan infections in humans and animals, as well as other conditions such as inflammatory diseases.

The formulations are preferably administered orally, in the form of rapid or controlled release tablets, microparticles, mini tablets, capsules and oral solutions or suspensions, or powders for the preparation thereof. In addition to the new isostructural 9-deoxo-9a-aza-9a-methyl-9a-homoerythromycin A pseudopolymorphs of the present invention as the active substance, oral preparations may optionally include various standard pharmaceutical carriers and excipients, such as binders, fillers, buffers, lubricants, glidants, disintegrants, odorants, sweeteners, surfactants and coatings. Some excipients may have multiple roles in the formulations, e.g., act as both binders and disintegrants.

Examples of pharmaceutically acceptable disintegrants for oral formulations useful in the present invention include, but are not limited to, starch, pre-gelatinized starch, sodium starch glycolate, sodium carboxymethylcellulose, croscarmellose sodium, microcrystalline cellulose, alginates, resins, surfactants, effervescent compositions, aqueous aluminum silicates and crosslinked polyvinylpyrrolidone.

Examples of pharmaceutically acceptable binders for oral formulations useful herein include, but are not limited to, acacia; cellulose derivatives, such as methylcellulose, carboxymethylcellulose, hydroxypropylmethylcellulose, hydroxypropylcellulose or hydroxyethylcellulose; gelatin, glucose, dextrose, xylitol, polymethacrylates, polyvinylpyrrolidone, sorbitol, starch, pre-gelatinized starch, tragacanth, xanthane resin, alginates, magnesium-aluminum silicate, polyethylene glycol or bentonite.

Examples of pharmaceutically acceptable fillers for oral formulations include, but are not limited to, lactose, anhydrolactose, lactose monohydrate, sucrose, dextrose, mannitol, sorbitol, starch, cellulose (particularly microcrystalline cellulose), dihydro- or anhydro-calcium phosphate, calcium carbonate and calcium sulfate.

Examples of pharmaceutically acceptable lubricants useful in the formulations of the invention include, but are not limited to, magnesium stearate, talc, polyethylene glycol, polymers of ethylene oxide, sodium lauryl sulfate, magnesium lauryl sulfate, sodium oleate, sodium stearyl fumarate, DL-leucine and colloidal silicon dioxide Examples of suitable pharmaceutically acceptable odorants for the oral formulations include, but are not limited to, synthetic aromas and natural aromatic oils such as extracts of oils, flowers, fruits and combinations thereof. Preferable are vanilla and fruit aromas, including banana, apple, sour cherry, peach and similar aromas. Their use depends on many factors, the most important being the organoleptic acceptability for the population that will be taking the pharmaceutical formulations.

Examples of suitable pharmaceutically acceptable dyes for the oral formulations include, but are not limited to, synthetic and natural dyes such as titanium dioxide, beta-carotene and extracts of grapefruit peel.

Examples of useful pharmaceutically acceptable coatings for the oral formulations, typically used to facilitate swallowing, modify the release properties, improve the appearance, and/or mask the taste of the formulations include, but are not limited to, hydroxypropylmethylcellulose, hydroxypropylcellulose and acrylate-methacrylate copolymers.

Suitable examples of pharmaceutically acceptable sweeteners for the oral formulations include, but are not limited to, aspartame, saccharin, saccharin sodium, sodium cyclamate, xylitol, mannitol, sorbitol, lactose and sucrose.

Suitable examples of pharmaceutically acceptable buffers include, but are not limited to, citric acid, sodium citrate, sodium bicarbonate, dibasic sodium phosphate, magnesium oxide, calcium carbonate and magnesium hydroxide.

Suitable examples of pharmaceutically acceptable surfactants include, but are not limited to, sodium lauryl sulfate and polysorbates.

Formulations of the isostructural 9-deoxo-9a-aza-9a-methyl-9a-homoerythromycin A pseudopolymorphs of the present invention can also be administered intravenously or intraperitoneally, by infusion or injection. Dispersions can also be prepared in a liquid carrier or intermediate, such as glycerin, liquid polyethylene glycols, triacetin oils, and mixtures thereof. To improve storage stability, such preparations may also contain a preservative to prevent the growth of microorganisms.

Pharmaceutical formulations suitable for injection or infusion may be in the form of a sterile aqueous solution, a dispersion or a sterile powder that contains the active ingredient, adjusted, if necessary, for preparation of such a sterile solution or dispersion suitable for infusion or injection. This may optionally be encapsulated into liposomes. In all cases, the final preparation must be sterile, liquid, and stable under production and storage conditions.

The liquid carrier or intermediate can be a solvent or liquid dispersive medium that contains, for example, water, ethanol, a polyol (e.g. glycerol, propylene glycol or the like), vegetable oils, non-toxic glycerine esters and suitable mixtures thereof. Suitable flowability may be maintained, by generation of liposomes, administration of a suitable particle size in the case of dispersions, or by the addition of surfactants. Prevention of the action of micro-organisms can be achieved by the addition of various antibacterial and antifungal agents, e.g. paraben, chlorobutanol, or sorbic acid. In many cases isotonic substances are recommended, e.g. sugars, buffers and sodium chloride to assure osmotic pressure similar to those of body fluids, particularly blood. Prolonged absorption of such injectable mixtures can be achieved by introduction of absorption-delaying agents, such as aluminium monostearate or gelatin.

Sterile injectable solutions can be prepared by mixing the 9-deoxo-9a-aza-9a-methyl-9a-homoerythromycin A isostructural pseudopolymorphs with an appropriate solvent and one or more of the aforementioned excipients, followed by sterile filtering. In the case of sterile powders suitable for use in the preparation of sterile injectable solutions, preferable preparation methods include drying in vacuum and lyophilization, which provide powdery mixtures of the isostructural pseudopolymorphs and desired excipients for subsequent preparation of sterile solutions.

The compounds of the present invention may also be used for the preparation of locally acting, topical formulations. Such formulations may also contain other pharmaceutically acceptable excipients, such as polymers, oils, liquid carriers, surfactants, buffers, preservatives, stabilizers, antioxidants, moisturizers, emollients, colorants and odorants.

Examples of pharmaceutically acceptable polymers suitable for such topical formulations include, but are not limited to, acrylic polymers; cellulose derivatives, such as carboxymethylcellulose sodium, methylcellulose or hydroxypropylcellulose; natural polymers, such as alginates, tragacanth, pectin, xanthan and cytosan.

Examples of suitable pharmaceutically acceptable oils which are so useful include but are not limited to, mineral oils, silicone oils, fatty acids, alcohols, and glycols.

Examples of suitable pharmaceutically acceptable liquid carriers include, but are not limited to, water, alcohols or glycols such as ethanol, isopropanol, propylene glycol, hexylene glycol, glycerol and polyethylene glycol, or mixtures thereof in which the pseudopolymorph is dissolved or dispersed, optionally with the addition of non-toxic anionic, cationic or non-ionic surfactants, and inorganic or organic buffers.

Suitable examples of pharmaceutically acceptable preservatives include, but are not limited to, various antibacterial and antifungal agents such as solvents, for example ethanol, propylene glycol, benzyl alcohol, chlorobutanol, quaternary ammonium salts, and parabens (such as methyl paraben, ethyl paraben, propyl paraben, etc.).

Suitable examples of pharmaceutically acceptable stabilizers and antioxidants include, but are not limited to, ethylenediaminetetraacetic acid (EDTA), thiourea, tocopherol and butyl hydroxyanisole.

Suitable examples of pharmaceutically acceptable moisturizers include, but are not limited to, glycerine, sorbitol, urea and polyethylene glycol.

Suitable examples of pharmaceutically acceptable emollients include, but are not limited to, mineral oils, isopropyl myristate, and isopropyl palmitate.

The use of dyes and odorants in topical formulations of the present invention depends on many factors of which the most important is organoleptic acceptability to the population that will be using the pharmaceutical formulations.

The therapeutically acceptable quantity of the 9-deoxo-9a-aza-9a-methyl-9a-homoerythromycin A isostructural pseudopolymorphs of the present invention administered varies, dependent on the selected compound, the mode of administration, treatment conditions, age and status of the patient or animal species, and is subject to the final decision of the physician, clinician or veterinary doctor monitoring the course of treatment.

Suitable oral and parenteral doses may vary within the range of from about 1 to about 200 mg per kg of body weight per day, preferably from about 5 to about 100 mg per kg of body weight and more preferably from about 5 to about 50 mg per kg of body weight per day. The 9-deoxo-9a-aza-9a-methyl-9a-homoerythromycin A pseudopolymorphs may be formulated in a single dosage form that contains from about 1 to about 3000 mg, preferably from about 100 to about 200 mg, and more desirably from about 150 to about 600 mg of the active substance per unit dose.

EXAMPLES

The isostructural pseudopolymorphs of the present invention were prepared as described in Examples 1-22 below, utilizing 9-deoxo-9a-aza-9a-methyl-9a-homoerythromycin A in various purities and crystalline forms, including anhydrous, hydrated and solvated forms, as substrates initially used therein. The various 9-deoxo-9a-aza-9a-methyl-9a-homoerythromycin A materials so utilized were commercially available or prepared in the manner disclosed in the prior art, to the extent that the conditions therein could be ascertained. In the experiments reported in the examples, the contents of the respective 9-deoxo-9a-aza-9a-methyl-9a-homoerythromycin A products were analyzed by HPLC, and residual solvent contents were determined by GC. Particle sizes and distributions were obtained by the Malvern Method. TGA and DSC measurements were performed on Perkin-Elmer instruments, SEM scans were performed on Jeol JFM-5800, and diffraction experiments were performed on Bruker-Nonius FR591/KappaCCD single crystal X-ray diffractometer and Philips X'PertPRO powder X-ray diffractometer equipped with Anton Paar TTK-100 humidity camera used for non-ambient data collection. The crystal structures of the several pseudopolymorphs thus produced are indicated in Table 1 below, and the conditions employed in their preparation are given in Tables 2 and 3.

Formulations containing the new isostructural pseudopolymorph of general formula I wherein x=1, y=0 of Examples 11 and 14 to 21 are described in Examples 23 and 24, and comparative data indicating the potential consistent bioavailability, and superior dissolution and stability properties of the new pseudopolymorph, relative to the commercial 9-deoxo-9a-aza-9a-methyl-9a-homoerythromycin A dihydrate product are given in Examples 25-26.

Preparation of the Pseudopolymorphs

Example 1

Preparation of Pseudopolymorph of Formula II (S=Acetone, x=1, y=0.5) by Precipitation from Acetone/Water (Method A)

The intermediate 9-deoxo-9a-aza-9a-homoerythromycin (9a-DeMet), obtained by method A of U.S. Pat. No. 4,328,334, was reacted with formic acid (1.8-2.5 mole/mole 9a-DeMet) and formalin (1-1.5 mole formaldehyde/mole 9 a-DeMet) in acetone (4-8 l/kg of the 9 a-DeMet material). The mixture was heated to its boiling point (about 56° C.) and stirred at that temperature for 4 hours.

The reaction mixture was thereafter cooled and activated charcoal was added thereto. After stirring the mixture was filtered, and the charcoal remaining on the filter was washed with acetone (0.5-2.0l/kg of the 9a-DeMet substrate). The combined acetone solution (both the filtrate and the wash) was then added to the water (10-20 l/kg of the 9a-DeMet). Product crystals were thus partially precipitated.

The resulting mixture was alkalized stepwise with 10% sodium hydroxide to a pH of 9.8, and then stirred at room temperature for 2 hours. The precipitate was a crystalline, isostructural pseudopolymorph of Formula I (II: S=acetone, x=1 and y=0.5). The precipitate was filtered, washed with an aqueous acetone solution (10% V/V) and dried at room temperature under atmospheric pressure to constant weight. A minimum of 0.7 mole of the isostructural pseudopolymorph was thus prepared. Upon single crystal x-ray diffraction analysis, the isostructural pseudopolymorph was characterized, identified as compound II in Table 1 below. The specific conditions utilized in the preparation of that pseudopolymorph are summarized in Table 2.

Example 2

Preparation of Pseudopolymorph of Formula Ie (S=iso-propanol, x=1.5, y=0.5) by Precipitation from Isopropanol/Water (Method A)

The native solution of 9-deoxo-9a-aza-9a-methyl-9a-homoerythromycin A formed as described in Example 1 from 9a-DeMet (1 mole), formic acid (1.8-2.5 mole/mole 9a-DeMet) and formalin (1-1.5 mole formaldehyde/mole 9a-DeMet) was added to isopropanol (4-8 l/kg of the 9a-DeMet material). The mixture was treated in the same manner as described in Example 1, i.e. it was heated to its boiling point and stirred at that temperature for 4 hours. The reaction mixture was then cooled and activated charcoal was added thereto. After stirring the mixture was filtered, and the charcoal remaining on the filter was washed with isopropanol (0.5-2.0 l/kg of the 9a-DeMet substrate). The combined isopropanol solution (both the filtrate and the wash) was then added to the water (10-20l/kg of the 9a-DeMet). Product crystals were thus precipitated.

The resulting mixture was alkalized stepwise with 10% sodium hydroxide to a pH of 9.8, and then stirred at room temperature for a further 2 hours. The precipitate was a crystalline, isostructural pseudopolymorph of Formula Ie, in the form of an isopropanol solvate (S=isopropanol, x=1.5 and y=0.5). The precipitate was filtered, washed with an aqueous isopropanol solution (10% V/V) and dried to constant weight at a temperature of 70° C. to 80° C., under a reduced pressure of 3 to 5 kPa. A minimum of 0.7 mole of the isostructural pseudopolymorph Ie was thus prepared. Upon single crystal x-ray diffraction analysis, the isostructural pseudopolymorph was characterized as identified in Table 1. The specific conditions utilized in the preparation are disclosed in Table 2.

Example 3

Preparation of Pseudopolymorph of Formula Id (S=n-propanol, x=1, y=0.5) by Precipitation from n-Propanol/Water (Method B)

Crude 9-deoxo-9a-aza-9a-methyl-9a-homoerythromycin A (5 g), having a water content of 5.7 mole %, was dissolved with stirring in 20 ml n-propanol and heated to a temperature of 40° C. to 50° C. The solution was treated with activated charcoal, filtered, and cooled to a temperature of 35° C. in a 2 hour period. The mixture was seeded with 0.25 g of the isostructural pseudopolymorph of the 9-deoxo-9a-aza-9a-methyl-9a-homoerythromycin A of the Formula Ie (S=n-propanol, x=1 and y=0.5), and cooled to 0° C. over a 24 hour period. The precipitate thus formed was the crystalline isostructural pseudopolymorph in the form of the n-propanol solvate. The precipitate was filtered, washed with cold n-propanol and dried to constant weight under a reduced pressure of 6 to 8 kPa and at a temperature of 40° C. 2.6 g of the isostructural pseudopolymorph Id characterized as identified in Table 1 was thus produced. The conditions utilized in the preparation are disclosed in Table 2.

Example 4

Preparation of Pseudopolymorph of Formula Ig (S=iso-butanol, x=1.25, y=0.5) by Precipitation from Isobutanol/Water (Method C)

Amorphous 9-deoxo-9a-aza-9a-methyl-9a-homoerythromycin A (5 g), having a water content of 3.8 mole %, was dissolved in 15 ml of isobutanol and heated to a temperature of 40° C. At that temperature, water was gradually added to the solution with stirring until slight turbidity formed. The solution was then gradually cooled to room temperature over 5 hours and allowed to stand at this temperature without stirring for a further 18 hours. The resulting precipitate was a crystalline, isostructural pseudopolymorph of Formula Ig, in the form of an isobutanol solvate (S=isobutanol, x=1.25 and y=0.5). The precipitate was filtered, washed with a cold aqueous solution of isobutanol (10% V/V) and dried to constant weight under atmospheric pressure and room temperature. 2.2 g of the pseudopolymorph Ig was thus prepared. Upon single crystal x-ray diffraction analysis, the crystal structure characterized in Table 1 was identified. The conditions of the preparative technique are disclosed in Table 2.

Example 5

Preparation of Pseudopolymorph of Formula Ic (S=Ethanol, x=1, y=0.5) by Precipitation from Ethanol/Water (Method D)

9-Deoxo-9a-aza-9a-methyl-9a-homoerythromycin A dihydrate (5 g; purity: USP 25) was dissolved in 35 ml of 96% ethanol. The stirred solution was heated to a temperature of 30° C. to 40° C., and subsequently added gradually, over a period of 2 hours, to 70 ml of water at 40° C. under seeding with 50 mg of the isostructural pseudopolymorph of Formula Ia in which x=1 and y=0. The mixture was then gradually cooled to 5° C. over a 24 hours period, with formation of a precipitate. The precipitate was filtered, washed with cold 96% ethanol, and dried to constant weight under atmospheric pressure and at a temperature of 0° C. to 10° C. 2.0 g of the pseudopolymorph Ic was obtained. Upon single crystal x-ray diffraction analysis, the isostructural pseudopolymorph Ic characterized in Table 1 was identified. The parameters of the preparation technique are disclosed in Table 2.

Examples 6-9

Preparation of the Pseudopolymorphs of Formulas Ij (S=Glycerol, x=1, y=0.5), Ik (S=Glycerol, x=1.5, y=0.5), Ib (S=Methanol, x=1.25, y=1), and Im (S=DMSO, x=1, y=0.5)

Analogous to the procedures outlined in Examples 3-5, crystalline isostructural pseudopolymorphs of Formula I in the form of the glycerol solvates Ij (S=glycerol, x=1 and y=0.5) and Ik (S=glycerol x=1.5 and y=0.5), the methanol solvate Ib (S=methanol, x=1.25 and y=1), and the dimethyl sulfoxide (DMSO) solvate Im (S=DMSO, x=1 and y=0.5) were prepared. Upon single crystal x-ray diffraction analysis, the respective pseudopolymorphs Ij, Ik, Ib, and Im were characterized as identified in Table 1. The preparative conditions are disclosed in Table 2.

Example 10

Preparation of the Pseudopolymorphs of Formulas Ih (S=1,2-Ethanediol, x=1, y=0.5) by Precipitation From 1,2-Ethanediol (Method E)

60 ml of a native solution of 9-deoxo-9a-aza-9a-methyl-9a-homoerythromycin A in ethyl acetate, prepared as described in of WO 01/00640, was diluted with a further 40 ml of ethyl acetate. The resulting mixture was alkalized stepwise with 10% NaOH solution to a pH of 9.8, and the layers separated. The ethyl acetate layer was washed with a saturated sodium chloride solution and treated with activated charcoal. The mixture was then filtered, and the charcoal remaining on the filter was washed with ethyl acetate (5 ml). To the combined ethyl acetate solution (both the filtrate and wash), 30 ml of 1,2-ethanediol was added. The ethyl acetate was then distilled out at atmospheric pressure. The residue after distillation was slowly cooled from 90° C. to 0° C. over a period of 30 hours.

The resulting precipitate was a crystalline isostructural pseudopolymorph of Formula Ih, in the form of a 1,2-ethanediol solvate (S=1,2-ethanediol, x=1 and y=0.5). The precipitate was filtered, washed with a cold aqueous solution of 1,2-ethanediol (10% V/V) and dried to constant weight under atmospheric pressure and at a temperature of 0° C. to 10° C. 3.4 g of the pseudopolymorph Ih was thus prepared. Upon single crystal x-ray diffraction analysis, the isostructural pseudopolymorph Ih was characterized, as indicated in Table 1. Preparative conditions are summarized in Table 2.

Example 11

Conversion of the Pseudopolymorph Il (S=Acetone, x=1, y=0.5) to Pseudopolymorph Ia (x=1, y=0)

A native dichloromethane solution of 9-deoxo-9a-aza-9a-methyl-9a-homoerythromycin A, prepared using the procedure described in U.S. Pat. No. 4,474,768, was converted to a crystalline isostructural pseudopolymorph of Formula Il (S=acetone, x=1 and y=0.5) using the procedures described in Examples 10 and 5 above, by methods E and D. The precipitate thus formed was filtered and washed with an aqueous acetone solution (10% V/V). Upon drying under a reduced pressure of 2 to 5 kPa and at a temperature of 70° C. to 80° C., 0.6 mole of pseudopolymorph Ia (x=1, y=0) was obtained (purity: USP 25). The crystal structure of pseudopolymorph Ia was characterized as identified in Table 1. The conditions employed are summarized in Table 2.

Examples 12-13

Preparation of the Pseudopolymorphs of Formulas If (S=n-Butanol, x=1.5, y=0.5) and Ii (S=1,3-Propanediol, x=1, y=0.5)

A native chloroform solution of 9-deoxo-9a-aza-9a-methyl-9a-homoerythromycin A, prepared according to the procedure described in U.S. Pat. No. 4,517,359, was converted to the pseudopolymorph If (S=n-butanol, x=1.5, and y=0.5). A native butyl acetate solution of 9-deoxo-9a-aza-9a-methyl-9a-homoerythromycin A, prepared according to the procedure disclosed in WO 99/58541, was converted to the pseudopolymorph Ii (S=1,3-propanediol, x=1 and y=0.5).

The pseudopolymorphs were prepared by analogy to the procedures described in Examples 3, 5, 10 and 11, by methods E and B as well as E and D. Upon single crystal x-ray diffraction analysis the pseudopolymorphs If and Ii were characterized, as indicated in Table 1. The conditions utilized are summarized in Table 2.

Example 14

Conversion of the Pseudopolymorph Il (S=Acetone, x=1, y=0.5) to Pseudopolymorph Ia (x=1, y=0)

The pseudopolymorph Il (S=acetone, x=1, y=0.5), obtained according to Example 1, was dried to constant weight under a reduced pressure of 0.1 kPa and at a temperature of 50° C. The resulting pseudopolymorph was characterized as Formula Ia (x=1 and y=0, Table 1). The yield was quantitative; purity: according to USP 25.

Example 15

Conversion of the Pseudopolymorph Ic (S=Ethanol, x=1, y=0.5) to Pseudopolymorph Ia (x=1, y=0)

The pseudopolymorph Ic (S=ethanol, x=1, y=0.5), prepared as described in Example 5, was dried to constant weight under a reduced pressure of 2 kPa and at a temperature of 80° C. The pseudopolymorph Ia obtained was identical in form and yield to that prepared in Example 14.

Example 16

Conversion of the Pseudopolymorph Ib (S=Methanol, x=1.25, y=1) to Pseudopolymorph Ia (x=1, y=0)

The crystalline pseudopolymorph Ib (S=methanol, x=1.25 and y=1), obtained according to Example 8, was dried to constant weight under a reduced pressure of 2 kPa and at a temperature of 80° C. The resulting pseudopolymorph Ia, characterized in Table 1, was identical in form and yield to that obtained in Example 14.

Example 17

Conversion of the Pseudopolymorph Id (S=n-Propanol, x=1, y=0.5) to Pseudopolymorph Ia (x=1, y=0)

The crystalline pseudopolymorph Id (S=n-propanol, x=1 and y=0.5), obtained according to Example 3, was dried to constant weight under a reduced pressure of 13 Pa and at a temperature of 80° C. The yield and purity of pseudopolymorph Ia (x=1 and y=0) thus produced were identical to those of Example 14.

Example 18

Conversion of the Pseudopolymorph Ie (S=iso-Propanol, x=1.5, y=0.5) to Pseudopolymorph Ia (x=1, y=0)

The crystalline pseudopolymorph Ie (S=isopropanol, x=1.5 and y=0.5), obtained according to Example 2, was subjected to sublimation under a reduced pressure of 1 Pa and at temperature of −95° C. until a product of constant weight was produced. The yield and purity of the pseudopolymorph Ia (x=1 and y=0) were identical to those of Example 14.

Example 19

Conversion of Crude
9-Deoxo-9a-aza-9a-methyl-9a-homoerythromycin A
to the Pseudopolymorph Ia (x=1, y=0)

The crude commercial 9-deoxo-9a-aza-9a-methyl-9a-homoerythromycin A (100 g) was suspended in 500 ml of water and acidified stepwise at room temperature during a period of 105 minutes to a pH of 5.2 using 10% hydrochloric acid. The resulting solution was then added dropwise for about 35 minutes to 1360 ml of approximately 3% acetone (formed by adding 1320 ml of water to 40 ml of acetone) at room temperature. To this solution, a 10% sodium hydroxide solution was added dropwise during 55 minutes at room temperature, until a pH of 9.8 was obtained. The mixture was then heated to 40° C., stirred at that temperature for 120 minutes and then cooled to 30° C. The precipitate was a crystalline isostructural pseudopolymorph Il (S=acetone, x=1, y=0.5). The precipitate was filtered, and washed twice with 30 ml of a 10% acetone solution. 234.1 g of wet pseudopolymorph Il (S=acetone, x=1, y=0.5) was thus obtained which, after drying to constant weight at 55° C. under a vacuum of 2.0 kPa, gave 93.5 g of the isostructural pseudopolymorph Ia (x=1 and y=0) of USP 25 purity (Batch 1).

Repeating this procedure twice (Batches 2 & 3) gave the pseudopolymorph Ia (x=1 and y=0) in yields of 92.5 g (Batch 2) and 93.8 g (Batch 3). Purity USP 25.

Example 20

Conversion of Crude
9-Deoxo-9a-aza-9a-methyl-9a-homoerythromycin A
to the Pseudopolymorph Ia (x=1, y=0)

The crude commercial 9-deoxo-9a-aza-9a-methyl-9a-homoerythromycin A (40 g) was suspended in 200 ml of water and acidified stepwise at room temperature for about 60 minutes to a pH of 5.5. The resulting solution was added dropwise to 600 ml of a 10% acetone solution (formed by adding 60 ml of acetone to 540 ml of water) at room temperature during 30 minutes. To this solution a 10% potassium carbonate solution was added dropwise at room temperature during a period of 80 minutes, until a pH of 9.8 was attained, by simultaneous seeding with 0.8 g of the pseudopolymorph Il (S=acetone, x=1 and y=0.5). The mixture was then stirred at room temperature for a further 15 minutes. The resulting crystals were filtered, washed twice with 20 ml of a 10% acetone solution and dried to constant weight under vacuum at 2.0 kPa and at a temperature of 75° C. 37.5 g of the isostructural pseudopolymorph Ia (x=1 and y=0) was thus obtained.

Example 21

Conversion of Pseudopolymorph Il (S=Acetone, x=1 and y=0.5) to the Pseudopolymorph Ia (x=1, y=0)

40 g of the isostructural pseudopolymorph Il (S=acetone, x=1 and y=0.5) was suspended in 200 ml water and acidified with 10% acetic acid at room temperature for about 60 minutes to a pH of 5.5. until the pseudopolymorph Il dissolved. The resulting solution was added dropwise to 600 ml of a 10% acetone solution (formed by adding 60 ml of acetone to 540 ml of water) at room temperature during 30 minutes. To this solution a 10% sodium hydroxide solution was added dropwise at room temperature during 80 minutes until a pH of 9.8 was attained, simultaneously by seeding with 0.4 g of the isostructural pseudopolymorph Il (S=acetone, x=1, y=0.5). The mixture was then stirred at room temperature for a further 15 minutes. The resulting crystals were filtered, washed twice with 20 ml of a 10% acetone solution and dried to constant weight under a vacuum of 2.0 kPa at 55° C. 35.5 g of the isostructural pseudopolymorph Ia (x=1 and y=0) was thus obtained.

Example 22

Reprecipitation of Pseudopolymorph Im (S=DMSO, x=1 and y=0.5).

2.0 g of the isostructural pseudopolymorph Im (S=DMSO, x=1 and y=0.5), obtained as described in Example 9, was dissolved in 10 ml of DMSO at a temperature of 50° C. Water was added dropwise to the solution at that temperature until it turned slightly turbid. The mixture was then cooled to room temperature over a two hour period, and kept at this temperature for a further 72 hours. The precipitated crystalline isostructural pseudopolymorph Im (S=DMSO, x=1 and y=0.5) was filtered, washed with cold water and dried to constant weight at atmospheric pressure and a temperature of 25° C. 1.1 g of the recrystallized pseudopolymorph Im (S=DMSO, x=1, y=0.5) was thus obtained.

TABLE 1

ESSENTIAL CRYSTALLOGRAPHIC DATA OF ISOSTRUCTURAL
9-DEOXO-9a-AZA-9a-METHYL-9a-HOMOERYTHROMYCIN A PSEUDOPOLYMORPHS OF THE INVENTION

| Unit Cell Parameters | Ia (x = 1, y = 0) | Ib (S = MeOH, x = 1.25, y = 1) | Ic (S = EtOH, x = 1, y = 0.5) | Id (S = n-PrOH, x = 1, y = 0.5) | Ie (S = i-PrOH, x = 1.5, y = 0.5) | If (S = n-BuOH, x = 1.5, y = 0.5) | Ig (S = i-BuOH, x = 1.25, y = 0.5) |
|---|---|---|---|---|---|---|---|
| 295° K. a/Å | 16.368(5)[1] | 16.546(3)[1] | | 16.32(2)[1] | 16.29410(10)[1] | | 16.166(8)[1] |
| b/Å | 16.301(3) | 16.185(6) | | 16.344(16) | 16.24440(10) | | 16.123(4) |
| c/Å | 18.408(5) | 18.511(7) | | 18.610(18) | 18.80600(10) | | 18.591(14) |
| $\beta$/° | 110.04(2) | 110.53(3) | | 108.88(9) | 108.5701(3) | | 107.68(14) |
| V/Å$^3$ | 4614.151 | 4642.273 | | 4698.005 | 4718.554 | | 4616.769 |
| 100° K. a/Å | | 16.3506(2)[1] | 16.1400(10)[1] | | 16.22990(10)[1] | 16.1580(10)[1] | 16.11940(10)[1] |
| b/Å | | 16.09370(10) | 16.1530(10) | | 16.05490(10) | 16.0190(10) | 15.97760(10) |
| c/Å | | 18.27800(10) | 18.2640(10) | | 18.38540(10) | 18.4570(10) | 18.5545(2) |

TABLE 1-continued

ESSENTIAL CRYSTALLOGRAPHIC DATA OF ISOSTRUCTURAL
9-DEOXO-9a-AZA-9a-METHYL-9a-HOMOERYTHROMYCIN A PSEUDOPOLYMORPHS OF THE INVENTION

| β/° | 109.4070(7) | 109.590(10) | | 108.7563(5) | 108.866(10) | 107.8143(6) |
|---|---|---|---|---|---|---|
| V/Å$^3$ | 4536.426 | 4485.977 | | 4536.263 | 4520.668 | 4549.575 |

| Unit Cell Parameters | Ih (S = 1,2-ethanediol, x = 1, y = 0.5) | Ii (S = 1,3-propanediol, x = 1; y = 0.5) | Ij (S = glycerol, x = 1; y = 0.5) | Ik (S = glycerol, x = 1.5; y = 0.5) | Il (S = acetone, x = 1; y = 0.5) | Im (S = DMSO, x = 1; y = 0.5; | 9-Deoxo-9a-aza-9a-methyl-9a-homoerythromycin A dihydrate[3] |
|---|---|---|---|---|---|---|---|
| 295° K. a/Å | 16.232(15)[1] | 16.001(6)[1] | 16.20(4)[1] | 16.303(6)[1] | 16.370(6)[1] | 16.349(3)[1] | 17.860 |
| b/Å | 16.213(10) | 16.21(2) | 16.253(13) | 16.304(4) | 16.235(7) | 16.304(3) | 16.889 |
| c/Å | 18.531(9) | 18.497(11) | 18.613(10) | 18.725(13) | 18.538(7) | 18.401(3) | 14.752 |
| β/°[2] | 109.63(3) | 109.20(6) | 109.30(5) | 108.968(15) | 109.09(3) | 108.948(12) | 90 |
| V/Å$^3$ | 4593.361 | 4530.817 | 4625.358 | 4706.922 | 4655.844 | 4639.085 | 4449.757 |
| 100° K. a/Å | 16.0909(2)[1] | 15.9690(2)1 | 16.0650(3)[1] | 16.1060(10)[1] | | 16.24550(20)[1] | |
| b/Å | 16.0674(2) | 15.9840(2) | 16.0171(3) | 16.1220(10) | | 16.14140(20) | |
| c/Å | 18.3287(2) | 18.5610(2) | 18.5618(3) | 18.4760(10) | | 18.16580(20) | |
| β/° | 109.1199(8) | 108.2430(8) | 108.5100(9) | 109.1290(10) | | 108.7695(7) | |
| V/Å$^3$ | 4477.274 | 4499.540 | 4529.142 | 4532.593 | | 4510.208 | |

[1] Data in parentheses indicate the statistical variation of the last digit of the reported parameter, e.g., the range of crystal axis a of Compound Ia was 16.363 to 16.373
[2] α and δ are 90° in each instance.
[3] Coded GEGJAD in Cambridge Crystallographic Database; Orthorhombic space group $P2_12_12_1$.

TABLE 2

CONDITIONS FOR PREPARATION OF ISOSTRUCTURAL
9-DEOXO-9A-AZA-9A-METHYL-9A-HOMOERYTHROMYCIN A PSEUDOPOLYMORPHS OF THE INVENTION

| Example | Starting Material | Solvent | Method | Dissolution Temperature °C. | Crystallization Temperature °C. | Drying Temperature/ Pressure °C./kPa | No. | FIG. No. |
|---|---|---|---|---|---|---|---|---|
| 1 | 9a-DeMet[1] | Acetone | A | 50 to 60 | room | 20 to 25/~100 | Il | 13 |
| 2 | 9a-DeMet[1] | iso-PrOH | A | 70 to 80 | room | 40/6 to 8 | Ie | 6 |
| 3 | Crude | n-PrOH | B | 40 to 50 | 50 to 0 | 40/6 to 8 | Id | 5 |
| 4 | Amorphous | iso-BuOH | C | 40 | 40 to 25 | 20 to 25/ ~ 100 | Ig | 8 |
| 5 | Dihydrate (USP 25) | Ethanol | D | 30 to 40 | 40 to 5 | 0 to 10/~100 | Ic | 4 |
| 6 | Dihydrate (USP 25) | 2-BuOH/glycerol | B | 50 | 50 to 25 | 20 to 25/~100 | Ik | 12 |
| 7 | Crude | tert-BuOH/glycerol | C | 40 | 40 to 25 | 0 to 10/~100 | Ij | 11 |
| 8 | Unstable monohydrate | Methanol | C | 20 to 30 | 30 to −5 | 20 to 25/~100 | Ib | 3 |
| 9 | Crude | Dimethyl sulfoxide | D | 30 to 40 | 40 to 25 | 20 to 25/3 to 5 | Im | 14 |
| 10 | Sol/EtOAc (WO 01/00640) | 1,2-Ethanediol | E + B | 90 | 90 to 0 | 0 to 10/~100 | Ih | 9 |
| 11 | Sol./CH$_2$Cl$_2$ (US 4474768) | Acetone | E + D | 50 to 60 | room | 80/2 to 5 | Ia | 2 |
| 12 | Sol./CHCl$_3$ (US 4517359) | n-BuOH | E + B | 50 | 50 to 0 | 0 to 10/~100 | If | 7 |
| 13 | Sol./n-BuOAc (WO 99/58541) | 1,3-Propanediol | E + D | 80 | 40 | 0 to 10/~100 | Ii | 10 |

[1] 9a-DeMet = 9-Deoxo-9a-aza-9a-homoerythromycin A

TABLE 3

FORMATION OF ISOSTRUCTURAL
9-DEOXO-9A-AZA-9A-METHYL-9A-HOMOERYTHROMYCIN A
PSEUDOPOLYMORPH Ia (x = 1, y = 0)

| Example | Starting Material | Method | Drying Temperature/ Pressure |
|---|---|---|---|
| 14 | Pseudopolymorph Il (S = acetone, x = 1, y = 0.5) | Drying | 50° C./0.1 kPa |
| 15 | Pseudopolymorph Ic (S = Ethanol, x = 1, y = 0.5) | Drying | 80° C./2 kPa |
| 16 | Pseudopolymorph Ib (S = Methanol, x = 1.25, y = 1) | Drying | 80° C./2 kPa |
| 17 | Pseudopolymorph Id (S = n-Propanol, x = 1, y = 0.5) | Drying | 80° C./13 Pa |
| 18 | Pseudopolymorph Ie (S = Isopropanol, x = 1.5, y = 0.5) | Sublimation | −95° C./1 Pa |
| 19 | Crude 9-deoxo-9a-aza-9a-methyl-9a-homoerythromycin A [1] | Drying In Situ Formed Wet Pseudopolymorph Il | 55° C./2.0 kPa |

TABLE 3-continued

FORMATION OF ISOSTRUCTURAL
9-DEOXO-9A-AZA-9A-METHYL-9A-HOMOERYTHROMYCIN A
PSEUDOPOLYMORPH Ia (x = 1, y = 0)

| Example | Starting Material | Method | Drying Temperature/ Pressure |
|---|---|---|---|
| 20 | Crude 9-deoxo-9a-aza-9a-methyl-9a-homoerythromycin A [1] | Drying In Situ Formed Wet Pseudopolymorph Il [2] | 75° C./2.0 kPa |
| 21 | Pseudopolymorph Il (S = acetone, x = 1, y = 0.5) [2] | Drying | 55° C./2.0 kPa |

[1] Pseudopolymorph Il (S = Acetone, x = 1, y = 0.5) prepared from crude 9-deoxo-9a-aza-9a-methyl-9a-homoerythromycin A and wet solvate dried in situ
[2] Pseudopolymorph Il (S = Acetone, x = 1, y = 0.5) crystallized using crystal seeding technique Formulations of the Pseudopolymorphs Example 23

Tablet Formulations

9-Deoxo-9a-aza-9a-methyl-9a-homoerythromycin A pseudopolymorph formulations were prepared by granulating isostructural pseudopolymorph (97%) of Examples 11 and 14-21 (x=1 and y=0 with starch, microcrystalline cellulose and croscarmellose sodium by standard granulation techniques. The dried granulates were homogenized with magnesium stearate, and tabletted using standard tabletting machines. Tablet cores were coated with a hydroxypropyl methylcellulose (HPMC) coating. The quantities of ingredients for 150, 200, 250, 300, 500 and 600 mg tablets are given in Table 4.

TABLE 4

TABLET FORMULATIONS OF
9-DEOXO-9A-AZA-9A-METHYL-9A-HOMOERYTHROMYCIN
A MONOHYDRATE PSEUDOPOLYMORPH (x = 1, y = 0)

| Formulation Component/Dose: | 150 mg | 200 mg | 250 mg | 300 mg | 500 mg | 600 mg |
|---|---|---|---|---|---|---|
| Isostructural pseudopolymorph of Formula I (x = 1, y = 0) (97%) | 158 | 210 | 263 | 316 | 526 | 632 |
| Starch | 16 | 20 | 25 | 30 | 50 | 60 |
| Microcrystalline cellulose | 85 | 115 | 140 | 170 | 280 | 340 |
| Croscarmellose sodium | 5 | 7 | 9 | 10 | 18 | 21 |
| Mg-stearate | 2 | 3 | 4 | 5 | 9 | 10 |
| HPMC (hydroxypropyl methylcellulose) | 8 | 11 | 14 | 16 | 27 | 32 |

Example 24

Topical Formulations

Water, co-solvents (glycerol, polyethylene glycol), preservatives (methyl and propylparaben), stasbilizer and gelling polymer are homogenized by standard technique to form an aqueous phase.

The isostructural pseudopolymorph Ia (x=1 and y=0) was added to such an aqueous phase and it was dispersed/dissolved. Oily components (such as liquid paraffin and cetyl alcohol), with the addition of emulsifier, were melted, and after being cooled, were mixed with the previously prepared aqueous phase. The final homogenization was carried out under reduced pressure. Odorant may be added to the last phase, i.e. homogeneous gel, and optionally its pH may be adjusted. A typical pseudopolymorph-containing formulation thus prepared is given in Table 5.

TABLE 5

TOPICAL FORMULATION CONTAINING
ISOSTRUCTURAL 9-DEOXO-9A-AZA-
9A-METHYL-9A-HOMOERYTHROMYCIN A
PSEUDOPOLYMORPH Ia

| Component | Dose (mg/ g) | Role |
|---|---|---|
| Isostructural 9-deoxo-9a-aza-9a-methyl-9a-homoerythromycin A Ia (x = 1, y = 0) | 100 | active substance |
| Glycerol | 100.00 | co-solvent |
| Isopropanol | 400.00 | co-solvent |
| PEG | 60.00 | co-solvent |
| Carbomer | 15.00 | gelling polymer |
| Citric acid | qs | pH adjustor |
| Polysorbate 40 | 10.00 | emulsifier |
| Methylparaben | 0.70 | preservative |
| Propylparaben | 0.30 | preservative |
| Disodium-EDTA | 0.5 | stabilizer |
| Liquid paraffin | 25.00 | oily component |
| Cetyl alcohol | 25.00 | oily component |
| Odorant | qs | |
| Water | up to 1 g | |

In these mixtures, a wide range of concentrations of the isostructural pseudopolymorphs of 9-deoxo-9a-aza-9a-methyl-9a-homoerythromycin A can be utilized; a preservative may also be incorporated in the preparation depending on the dosage form (i.e., multidose or monodose).

Superior Properties of the Isostructural Pseudopolymorph of the Invention

Example 25

Figure 17:
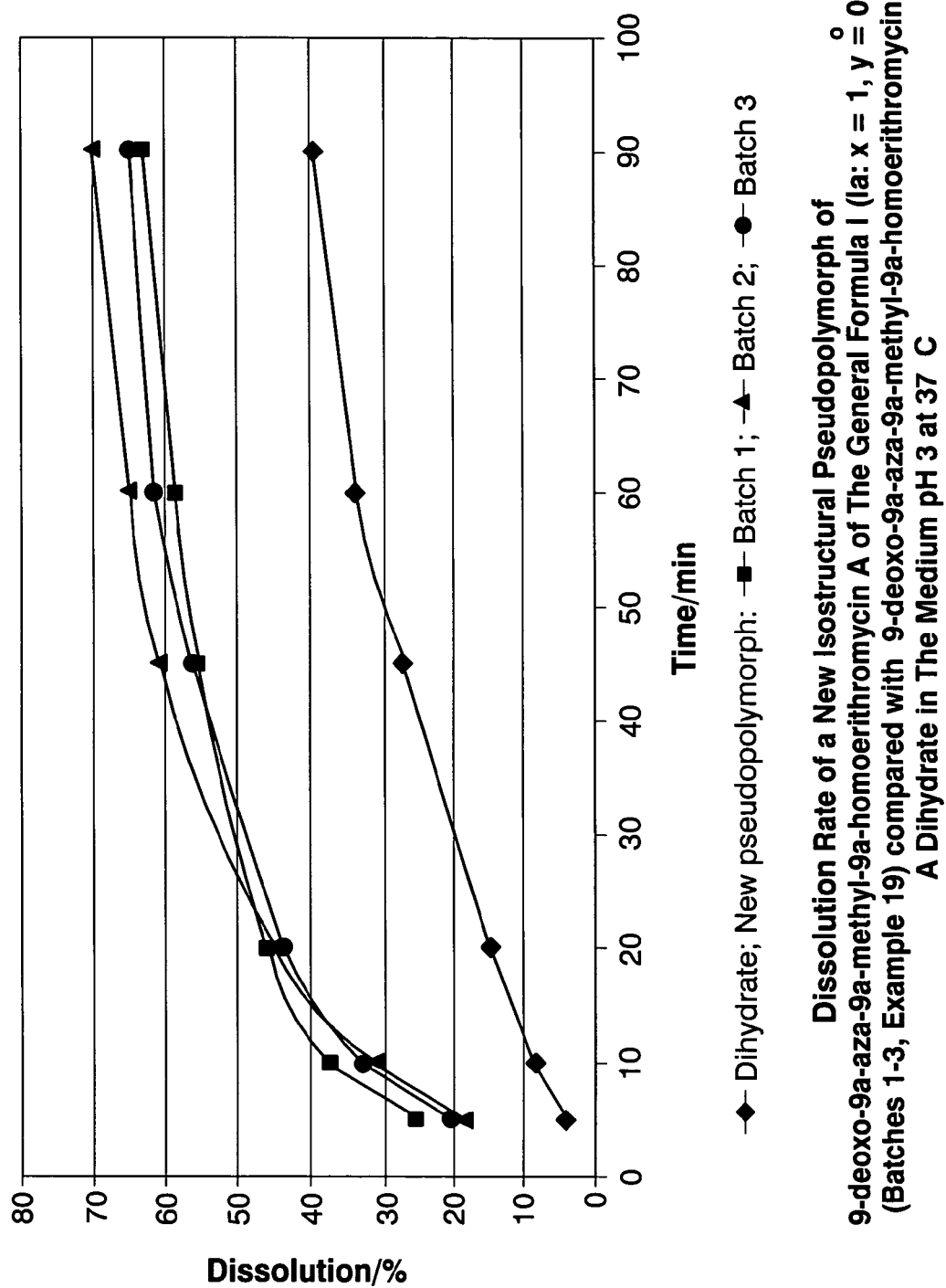
FIG. 17 is a graph comparing the dissolution rates of the pseudopolymorph of the invention and the known 9-deoxo-9a-aza-9a-methyl-9a-homoerythromycin A dihydrate, at pH 3 and 37° C.
Figure 18:
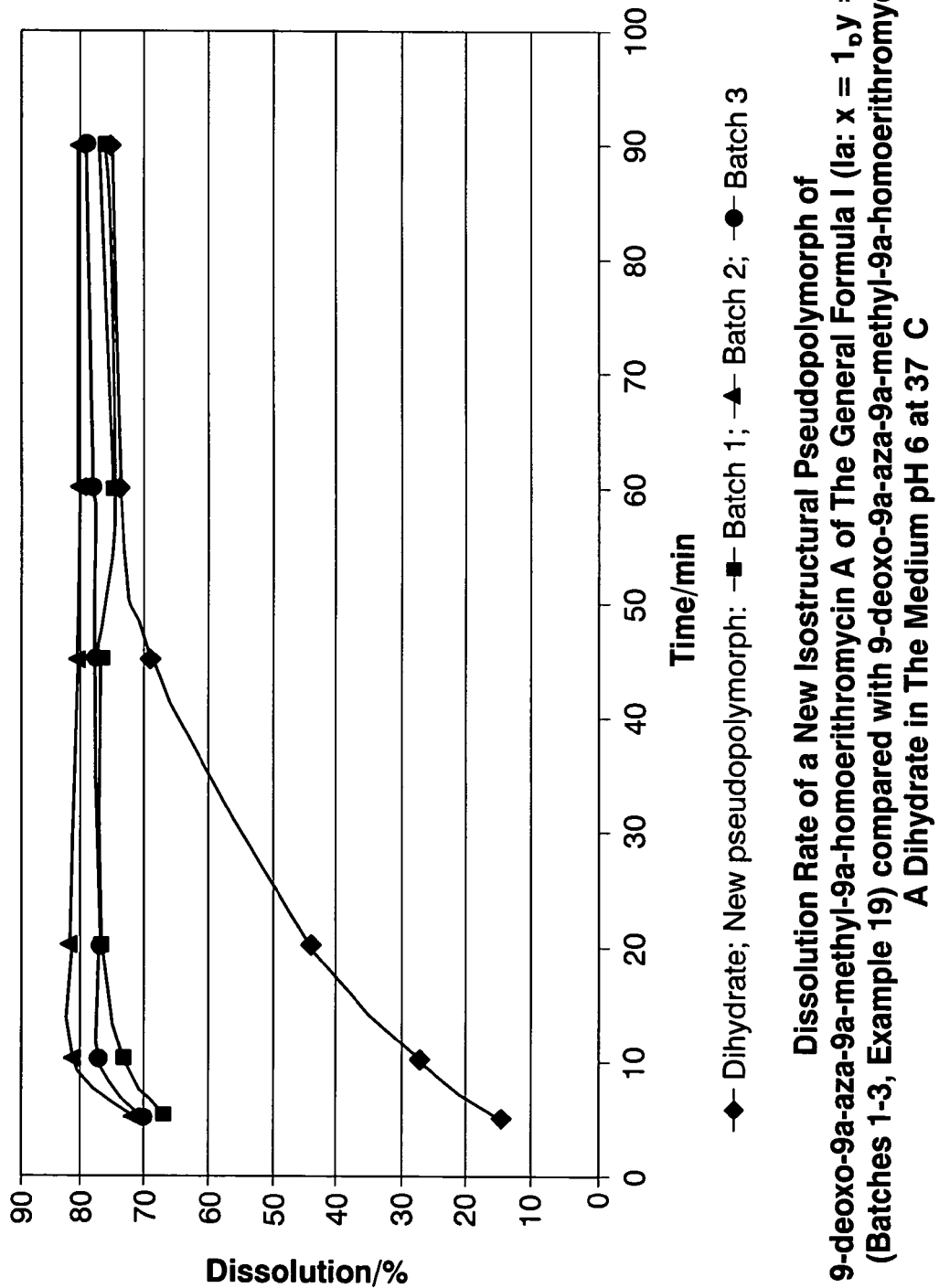
FIG. 18 is a graph comparing the dissolution rates of the pseudopolymorph of the invention and the known 9-deoxo-9a-aza-9a-methyl-9a-homoerythromycin A dihydrate, at pH 6 and 37° C.

Dissolution Profiles of the New Pseudopolymorph of the Invention vs. Commercial 9-deoxo-9a-aza-9a-methyl-9a-homoerythromycin A Dihydrate In order to compare the behavior in vitro of the 9-deoxo-9a-aza-9a-methyl-9a-homoerythromycin A pseudopolymorph Ia of the invention with the commercial 9-deoxo-9a- aza-9a-methyl-9a-homoerythromycin A dihydrate product, dissolution profiles have been determined at pH 3 and pH 6, at 37° C. For comparison, 3 batches of 9-deoxo-9a-aza-9a-methyl-9a-homoerythromycin A pseudopolymorph Ia from Example 19 above were used. The comparative dissolution profiles were determined by USP Method 2, PharmaTest Dissolution Tester, PTW SII; the content of dissolved 9-deoxo-9a-aza-9a-methyl-9a-homoerythromycin A was measured by HPLC. The data thus obtained are set forth in Table 6 below, and plotted in FIGS. 17 and 18.

TABLE 6

PERCENT OF 9-DEOXO-9A-AZA-9A-METHYL-9A-HOMOERYTHROMYCIN A PSEUDOPOLYMORPH Ia AND COMMERCIAL 9-DEOXO-9a-AZA-9a-METHYL-9a-HOMOERYTHROMYCIN A DIHYDRATE PRODUCT DISSOLVED

| Time | Commercial 9-deoxo-9a-aza-9a-methyl-9a-homoery-thromycin A Dihydrate | | 9-deoxo-9a-aza-9a-methyl-9a-homoery-thromycin A Pseudo-polymorph Ia (Example 19, Batch 1) | | 9-deoxo-9a-aza-9a-methyl-9a-homoery-thromycin A Pseudo-polymorph Ia (Example 19, Batch 2) | | 9-deoxo-9a-aza-9a-methyl-9a-homoery-thromycin A Pseudo-polymorph Ia (Example 19, Batch 3) | |
|---|---|---|---|---|---|---|---|---|
| Minutes | pH 3 | pH 6 | pH 3 | pH 6 | pH 3 | pH 6 | pH 3 | pH 6 |
| 5 | 3.9 | 14.5 | 25.1 | 67.0 | 18.5 | 71.7 | 21.1 | 70.2 |
| 10 | 8.1 | 27.3 | 37.1 | 73.2 | 30.7 | 81.4 | 32.4 | 77.3 |
| 20 | 14.6 | 44.2 | 45.8 | 76.7 | 45.1 | 81.6 | 43.3 | 77 |
| 45 | 26.7 | 69.1 | 55.5 | 76.7 | 60.9 | 80.4 | 56 | 77.6 |
| 60 | 33.3 | 73.7 | 58.3 | 74.5 | 64.8 | 79.9 | 61.1 | 78 |
| 90 | 39.1 | 75.0 | 62.9 | 75.8 | 70 | 80 | 64.7 | 79.2 |

In addition to the above data, the intrinsic dissolution rates (IDR's) for the new pseudopolymorph of the invention and the commercial dihydrate, at pH 3 and pH 6 and 37° C., were determined by Intrinsic Dissolution Tester, Van Kel Type. The IDR for the new pseudopolymorph was about 2.5-2.8 mg min$^{-1}$ cm$^{-2}$, about 40 to 50% higher than the IDR of the prior art 9-deoxo-9a-aza-9a-methyl-9a-homoerythromycin A dihydrate (about 1.8 mg min$^{-1}$cm$^{-2}$).

Example 26

Comparison of Dissolution Profiles of Three Batches of the New Pseudopolymorph of the Invention and Commercial 9-deoxo-9a-aza-9a-methyl-9a-homoerythromycin A Dihydrate In order to further assess the data from Table 6, similarity factors (f2) were calculated according to the method described in *Note for Guidance on the Investigation of Bioavailability and Bioequivalence* (*EMEA, December* 1998, *London*) for the dissolution profiles of the two species (9-deoxo-9a-aza-9a-methyl-9a-homoerythromycin A, pseudopolymorph Ia of the present invention, and commercial 9-deoxo-9a-aza-9a-methyl-9a-homoerythromycin A dihydrate).

A similarity factor (f2) of between 50 and 100 suggests that two dissolution profiles compared are similar and suggests that they have similar bioavailability. On the other hand, f2 values below 50 indicate significant differences in two dissolution profiles and hence in their relative bioavailability. A comparison of the calculated f2 values for the respective pairs of the three batches of the 9-deoxo-9a-aza-9a-methyl-9a-homoerythromycin A pseudopolymorph Ia (x=1, y=0) prepared according to Example 19 are given in Table 7. Also given is a comparison of the f2 values for each batch of Example 19 as compared with the commercial 9-deoxo-9a-aza-9a-methyl-9a-homoerythromycin A dihydrate product.

TABLE 7

CALCULATED SIMILARITY FACTORS FOR THE 9-DEOXO-9a-AZA-9a-METHYL-9a-HOMOERYTHROMYCIN A PSEUDOPOLYMORPH Ia OF EXAMPLE 19 AND THE COMMERCIAL 9-DEOXO-9a-AZA-9a-METHYL-9a-HOMOERYTHROMYCIN A DIHYDRATE PRODUCT

| | f2 Value Comparison Between Batches of 9-deoxo-9a-aza-9a-methyl-9a-homoerythromycin A Pseudopolymorph Ia (x = 1, y = 0) of Example 19 | | | f2 Value Comparison Between Batches of 9-deoxo-9a-aza-9a-methyl-9a-homoerythromycin A Pseudopolymorph Ia (x = 1, y = 0) of Example 19 and the Commercial 9-deoxo-9a-aza-9a-methyl-9a-homoerythromycin A Dihydrate | | |
|---|---|---|---|---|---|---|
| Similarity factor (f2) | Batch 1 vs. Batch 2 | Batch 1 vs. Batch 3 | Batch 2 vs. Batch 3 | Dihydrate vs. Batch 1 | Dihydrate vs. Batch 2 | Dihydrate vs. Batch 3 |
| pH = 3 | 61.3 | 74.7 | 71.3 | 28.6 | 27.5 | 29.4 |
| pH = 6 | 63.1 | 75.4 | 75.3 | 25 | 22.2 | 23.7 |

According to Table 7, Batches 1, 2, and 3 of the 9-deoxo-9a-aza-9a-methyl-9a-homoerythromycin A pseudopolymorph Ia (x=1, y=0) of Example 19 have similar dissolution profiles (and hence bioavailability), whereas the dissolution profiles of the dihydrate relative to each batch of the new pseudopolymorph of the invention are dissimilar (and hence the bioavailability would be expected to significantly differ). Given these properties, it would be expected that the pseudopolymorphs of the invention would have consistent, superior release characteristics, particularly with respect to immediate or controlled release formulations

Example 27
Solid State Stability of New Pseudopolymorph Ia of the Invention The solid state stability of the 9-deoxo-9a-aza-9a-methyl-9a-homoerythromycin A pseudopolymorph Ia (x=1, y=0) was determined by measuring the solid state x-ray powder diffraction pattern for this material at four different percent relative humidities (% RH), ranging from 5% RH to 75% RH, and at five different temperatures, increasing from 30° C. to 75° C. using Philips X'PertPRO powder X-ray diffractometer equipped with Anton Paar TTK-100 humidity camera used for non-ambient data collection. The results are shown in FIG. 19. As illustrated, no phase-transitions occur, i.e., there is no interconversion of the 9-deoxo-9a-aza-9a-methyl-9a-homoerythromycin A pseudopolymorph Ia (x=1, y=0) to any other form, as either the temperature increases or the relative humidity increases.

Example 28

Figure 20:
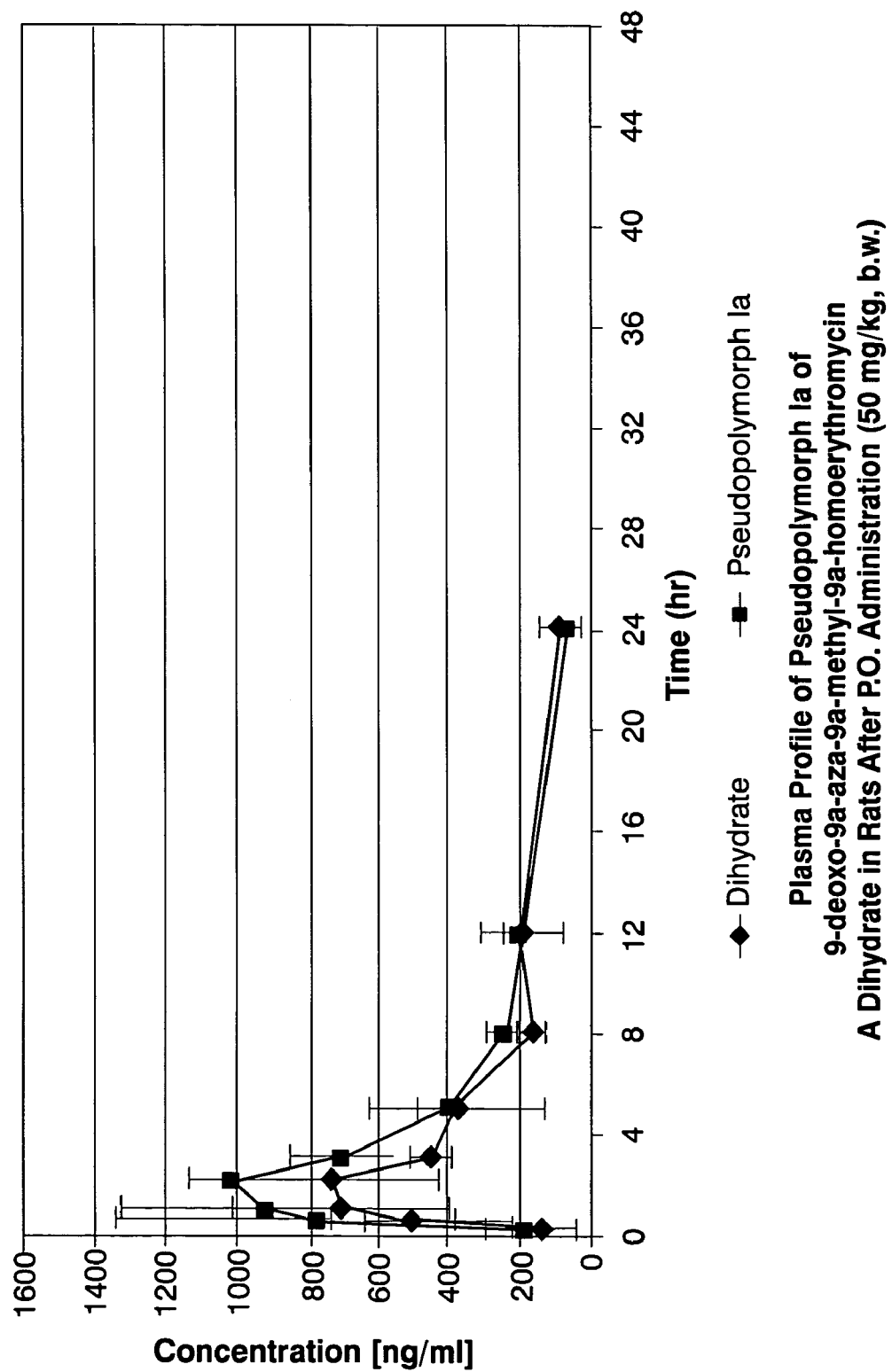
FIG. 20 is a graph illustrating the plasma profile of the pseudopolymorph of 9-deoxo-9a-aza-9a-methyl-9a-homoerythromycin A of Formula I (compound Ia: x=1, y=0) and 9-deoxo-9a-aza-9a-methyl-9a-homoerythromycin dihydrate in rats after per os administration (50 mg/kg, b.w.)
Figure 21:
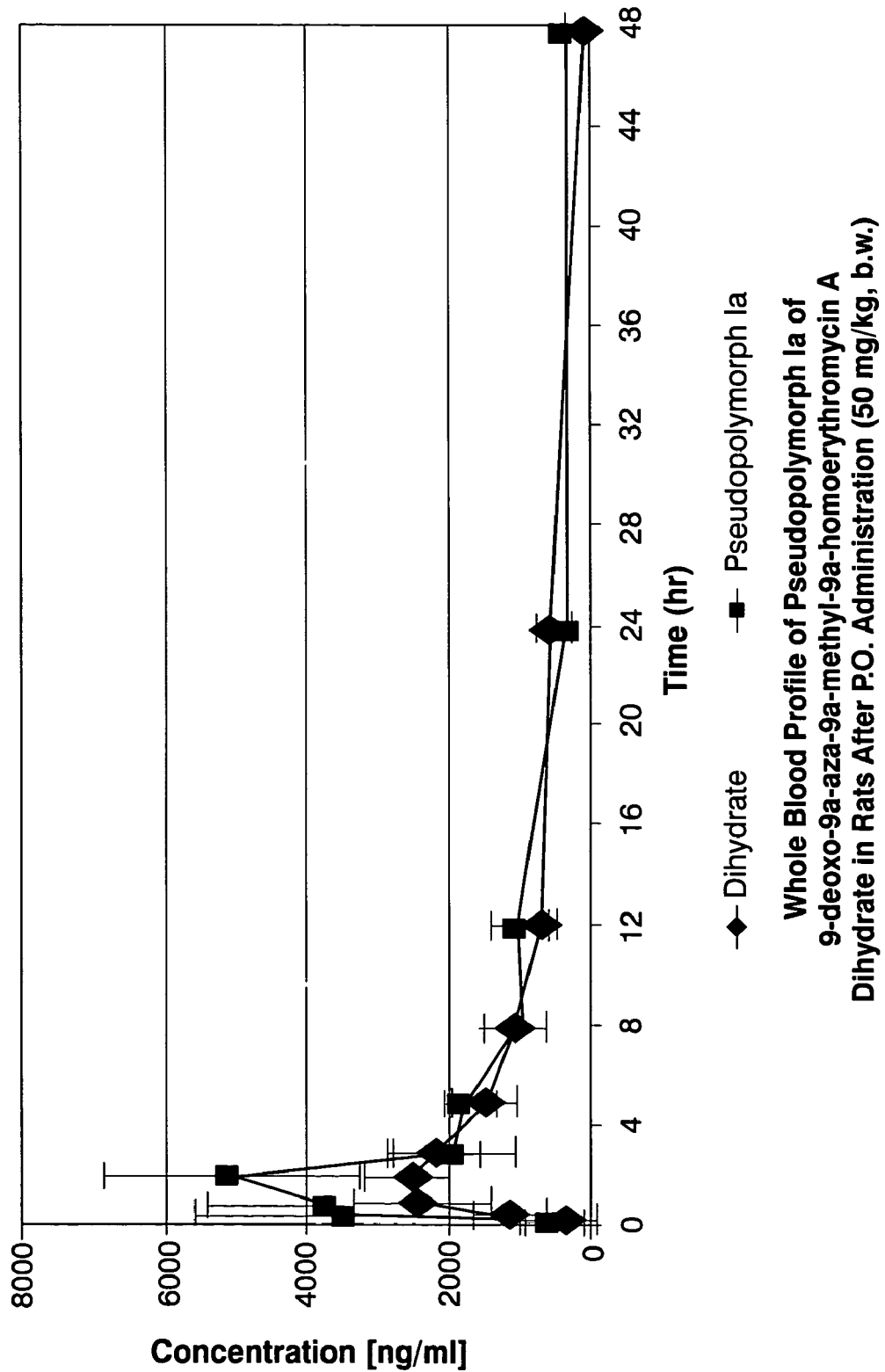
FIG. 21 is a graph illustrating the whole blood profile of the pseudopolymorph of 9-deoxo-9a-aza-9a-methyl-9a-homoerythromycin A of Formula I (compound Ia: x=1, y=0) and 9-deoxo-9a-aza-9a-methyl-9a-homoerythromycin dihydrate in rats after per os administration (50 mg/kg, b.w.)

In Vivo Pharmacokinetic Profiles of New Pseudopolymorph Ia of the Invention vs. Commercial 9-deoxo-9a-aza-9a-methyl-9a-homoerythromycin A Dihydrate In order to compare the behavior in vivo of the 9-deoxo-9a-aza-9a-methyl-9a-homoerythromycin A pseudopolymorph Ia of the invention with commercial 9-deoxo-9a-aza-9a-methyl-9a-homoerythromycin A dihydrate product, plasma and whole blood concentration time curves have been determined in rats after per os administration at a concentration of 50 mg/kg body weight. 32 animals were studied using a cross-over experimental design experiment. A non-compartmental analysis was used to determine the concentrations of the respective materials in whole blood and plasma as a function of time. The data thus obtained are set forth in FIGS. 20 and 21.

The pharmacokinetic parameters for the 9-deoxo-9a-aza-9a-methyl-9a-homoerythromycin A pseudopolymorph Ia of the invention and the commercial 9-deoxo-9a-aza-9a-methyl-9a-homoerythromycin A dihydrate product in whole blood and in plasma in rats following a per os dose of 50 mg/kg body weight are set forth in Table 8 below.

TABLE 8

IN VIVO PHARMACOKINETIC PARAMETERS FOR
9-DEOXO-9A-AZA-9A-METHYL-9A-HOMOERYTHROMYCIN A
PSEUDOPOLYMORPH IA AND COMMERCIAL
9-DEOXO-9A-AZA-9A-METHYL-9A-HOMOERYTHROMYCIN A DIHYDRATE

|  | 9-deoxo-9a-aza-9a-methyl-9a-homoerythromycin A dihydrate | | 9-deoxo-9a-aza-9a-methyl-9a-homoerythromycin A pseudopolymorph Ia | |
|---|---|---|---|---|
|  | Whole Blood | Plasma | Whole Blood | Plasma |
| $C_{max}$ (ng/ml) | 2569.0 ± 606.0 | 734.5 ± 307.2 | 5061.0 ± 1804.4 | 1005.5 ± 131.0 |
| $T_{max}$ (hr) | 2 | 2 | 2 | 2 |
| $AUC_{(0-12)}$ (nghr/ml) | 16721.1 | 3997.9 | 21203.9 | 5147.7 |
| $AUC_{(0-24)}$ (nghr/ml) | 24442.8 | 5755.6 | 29272.6 | 6853.2 |
| $AUC_{(0-48)}$ (nghr/ml) | 31696.6 |  | 35659.0 |  |

As indicated in Table 8, higher concentrations of the 9-deoxo-9a-aza-9a-methyl-9a-homoerythromycin A pseudopolymorph Ia of the invention as compared with the commercial 9-deoxo-9a-aza-9a-methyl-9a-homoerythromycin A dihydrate product are observed in both whole blood and plasma following per os administration in rats. The greatest concentration difference between the two 9-deoxo-9a-aza-9a-methyl-9a-homoerythromycin A products is observed after 2 hours ($T_{max}$).

Higher AUC values were particularly observed for the 9-deoxo-9a-aza-9a-methyl-9a-homoerythromycin A pseudopolymorph Ia during the first 12 hours following administration. The calculated AUC value for the first 0-12 hours, $AUC_{(0-12)}$, is surprisingly approximately 20% higher for the 9-deoxo-9a-aza-9a-methyl-9a-homoerythromycin A pseudopolymorph Ia relative to the commercial 9-deoxo-9a-aza-9a-methyl-9a-homoerythromycin A dihydrate product in both whole blood and plasma.

These results suggest faster absorption, higher bioavailability and more rapid distribution of the 9-deoxo-9a-aza-9a-methyl-9a-homoerythromycin A pseudopolymorph Ia into cells and/or tissues relative to the commercial 9-deoxo-9a-aza-9a-methyl-9a-homoerythromycin A dihydrate product.

Example 29

Figure 22:
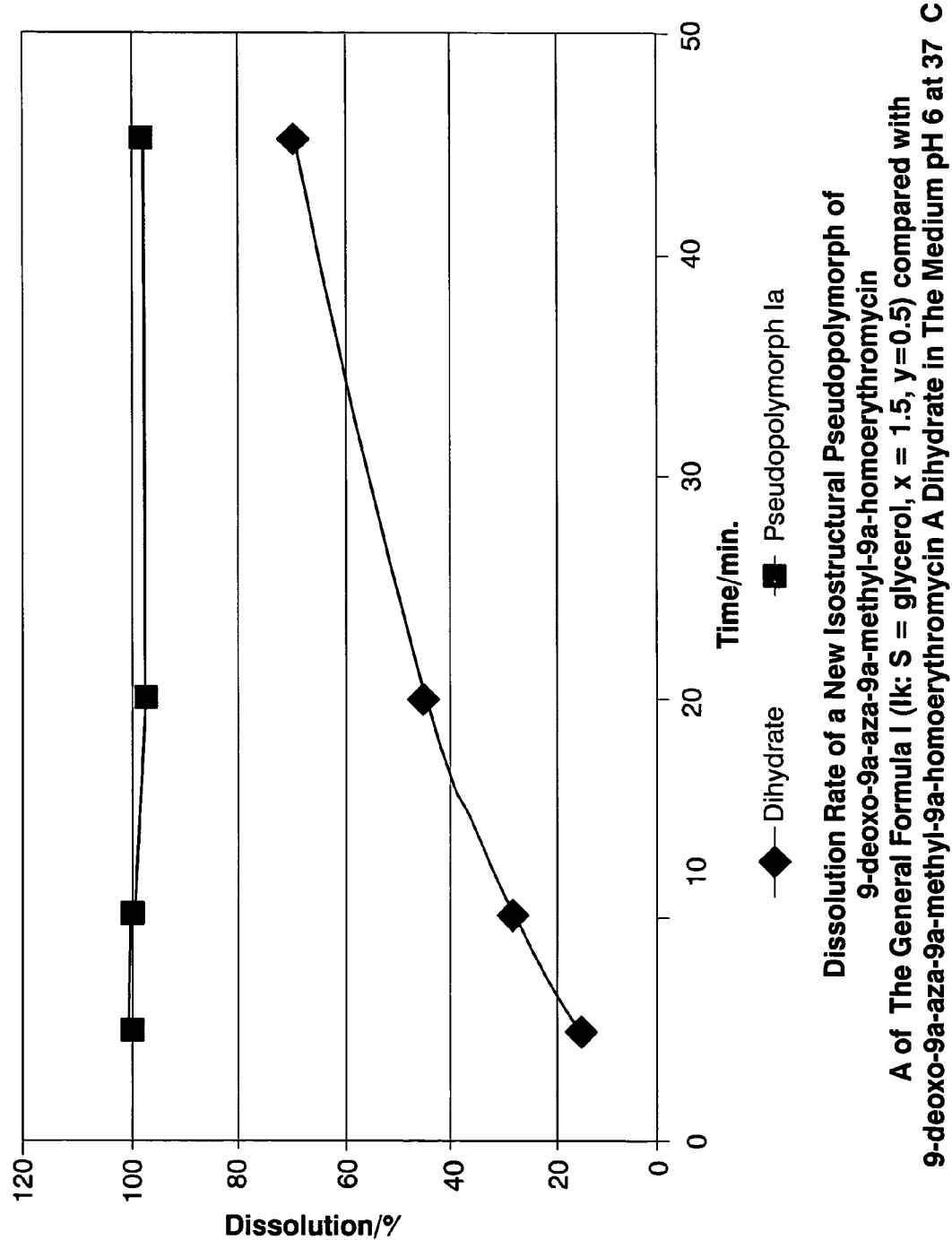
FIG. 22 is a graph comparing the dissolution rates of the pseudopolymorph Ik of the invention and the known 9-deoxo-9a-aza-9a-methyl-9a-homoerythromycin A dihydrate, at pH 6 and 37° C.

Dissolution Profiles of the New Pseudopolymorph Ik (S=glycerol; x=1.5, y=0.5) of the Invention vs. Commercial 9-deoxo-9a-aza-9a-methyl-9a-homoerythromycin A Dihydrate In order to compare the behavior in vitro of the 9-deoxo-9a-aza-9a-methyl-9a-homoerythromycin A pseudopolymorph Ik of the invention with the commercial 9-deoxo-9a-aza-9a-methyl-9a-homoerythromycin A dihydrate product, dissolution profiles have been determined at pH 6, at 37° C. For comparison, 9-deoxo-9a-aza-9a-methyl-9a-homoerythromycin A pseudopolymorph Ik from Example 6 above was used. The comparative dissolution profiles were determined by USP Method 2, PharmaTest Dissolution Tester, PTW SII; the content of dissolved 9-deoxo-9a-aza-9a-methyl-9a-homoerythromycin A was measured by HPLC. The data thus obtained are set forth in Table 9 below, and plotted in FIG. 22.

TABLE 9

PERCENT OF 9-DEOXO-9A-AZA-9A-METHYL-9A-HOMOERYTHROMYCIN A PSEUDOPOLYMORPH Ik AND COMMERCIAL 9-DEOXO-9a-AZA-9a-METHYL-9a-HOMOERYTHROMYCIN A DIHYDRATE PRODUCT DISSOLVED

| Time Minutes | Commercial 9-deoxo-9a-aza-9a-methyl-9a-homoerythromycin A Dihydrate pH 6 (37° C.) | 9-deoxo-9a-aza-9a-methyl-9a-homoerythromycin A Pseudopolymorph Ik (Example 6) pH 6 (37° C.) |
| --- | --- | --- |
| 5 | 14.5 | 99.8 |
| 10 | 27.3 | 99.9 |
| 20 | 44.2 | 97.1 |
| 45 | 69.1 | 97.6 |

What is claimed is:

1. A substantially pure isostructural pseudopolyrnorph of 9-deoxo-9a-aza-9a-methyl-9a-homoerythromycin A, having the Formula I:

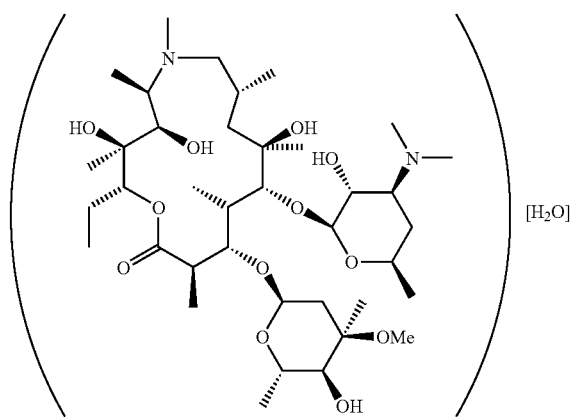

(I)

the pseudopolymorph being characterized by the monoclinic space group $P2_1$ and average unit cell parameters at 22° C. of:
a=16.368(5) Å, b=16.301(3) Å, c=18.408(5)Å, and
angles between the crystal axes of $\alpha=\gamma=90°$ and $\beta=110.04(2)°$.

2. A pharmaceutical composition comprising an active pharmaceutical ingredient that is a substantially pure isostructural pseudopolymorph of 9-deoxo-9a-aza-9a-methy-9a-homoerythromycin A having the Formula I:

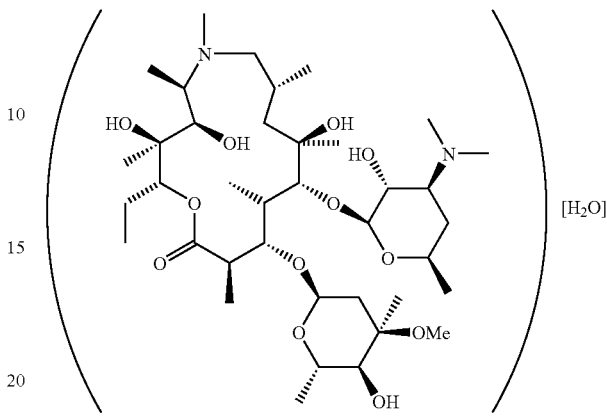

(I)

the pseudopolymorph being characterized by the inonoclinic space group $P2_1$ and average unit cell parameters at 22° C. of:
a =16.368(5) Å,
b =16.301(3) Å,
c =18.408(5) Å,
$\alpha=\gamma=90°$, and
$\beta=110.04(2)°$,
in combination with a pharmaceutically acceptable carrier wherein the pseudopolymorph retains the monoclinic space group and average unit cell parameters when combined with the pharmaceutically acceptable carrier, and wherein the pharmaceutical composition is a tablet or powder.

3. The substantially pure isostructural pseudopolymorph of 9-deoxo-9a-aza-9a-methyl-9a-hoxnoerythromycin A as claimed in claim 1, which contains not more than 10% of another compound.

4. The substantially pure isostructural pseudopolymorph of 9-deoxo-9a-aza-9a-methyl-9a-homoerythromycin A as claimed in claim 3, which contains not more than 10% of some other crystalline or amorphous form of 9-deoxo-9a-aza-9a-methyl-9a-homoerythromycin A.

5. The substantially pure isostructural pseudopolymorph of 9-deoxo-9a-aza-9a-methyl-9a-homoerythromycin A as claimed in claim 3, which contains not more than 5% of another compound.

6. The substantially pure isostructural pseudopolymorph of 9-deoxo-9a-aza-9a-methyl-9a-homoerytliromycin A as claimed in claim 3, which contains not more than 5% of some other crystalline or amorphous form of 9-deoxo-9a-aza-9a-methyl-9a-homoerythromycin A.

* * * * *